United States Patent
Trbojevic

(10) Patent No.: US 8,173,981 B2
(45) Date of Patent: May 8, 2012

(54) GANTRY FOR MEDICAL PARTICLE THERAPY FACILITY

(75) Inventor: Dejan Trbojevic, Wading River, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 363 days.

(21) Appl. No.: 12/511,621

(22) Filed: Jul. 29, 2009

(65) Prior Publication Data
US 2010/0038552 A1     Feb. 18, 2010

Related U.S. Application Data

(63) Continuation-in-part of application No. 11/433,644, filed on May 12, 2006, now Pat. No. 7,582,886.

(60) Provisional application No. 61/227,211, filed on Jul. 21, 2009.

(51) Int. Cl.
*H01J 37/08* (2006.01)
*A61N 5/10* (2006.01)

(52) U.S. Cl. .............. 250/493.1; 250/492.3; 250/398

(58) Field of Classification Search ........... 250/493.1, 250/492.3, 398
See application file for complete search history.

(56) References Cited

U.S. PATENT DOCUMENTS

| | | | |
|---|---|---|---|
| 4,870,287 A | 9/1989 | Cole et al. | |
| 5,260,581 A | 11/1993 | Lesyna et al. | |
| 5,585,642 A * | 12/1996 | Britton et al. | 250/492.3 |
| 7,345,291 B2 | 3/2008 | Kats | |

OTHER PUBLICATIONS

D. Trbojevic et al., A Dramatically Reduced Size in the Gantry Design for the Proton-Carbon Therapy, Jun. 2006, 10th Biennial European Particle Accelerator Conference.*
D. Trbojevic et al., "Design of a Nonscaling Fixed Field Alternating Gradient Accelerator," Physical Review Special Topics—Accelerators and Beams 8.050101, May 19, 2005.
R. Gupta et al., "Test Results of HTS Coils and an R&D Magnet for RIA," Particle Accelerator Conference, Knoxville, TN, May 16-20, 2005.
D. Harding et al., "Magnet Design Issues and Discussion," Presentation at FFAG Workshop at Fermilab, Apr. 3, 2005.
R. Fuchs et al., "The Heavy Ion Gantry of the HICAT Facility," Publication Date Unknown.
B. Parker, "The Serpentine Coil Design for BEPC-II Superconducting IR Magnets," Presentation at IHEP/CAS, Beijing, P.R. China, Jan. 12, 2004.
K. Halbach, "Design of Permanent Multipole Magnets with Oriental Rare Earth Cobalt Material," Nuclear Instruments and Methods, 169, pp. 1-10 (1980).
Ueno et al., Multi-Orbit Synchrotron with FFAG Focusing for Acceleration of High Intensity Hadron Beams, Proceedings of the 1999 Particle Accelerator Conference, New York, 1999, pp. 2271-2273.

* cited by examiner

*Primary Examiner* — David A Vanore
(74) *Attorney, Agent, or Firm* — Dorene M. Price

(57) ABSTRACT

A particle therapy gantry for delivering a particle beam to a patient includes a beam tube having a curvature defining a particle beam path and a plurality of fixed field magnets sequentially arranged along the beam tube for guiding the particle beam along the particle path. In a method for delivering a particle beam to a patient through a gantry, a particle beam is guided by a plurality of fixed field magnets sequentially arranged along a beam tube of the gantry and the beam is alternately focused and defocused with alternately arranged focusing and defocusing fixed field magnets.

17 Claims, 18 Drawing Sheets

Non-Scaling FFAG Gantry - Basic Cell
Betatron Functions in the Basic Cell

Estimated Beam Pipe Size and Magnetic Field at the Major Bend a Combined Function Magnet with Defocusing Gradient Estimated Beam Pipe Size and Magnetic Field Values at the Opposite Bend Focusing Combined Function Magnet

US 8,173,981 B2

GANTRY FOR MEDICAL PARTICLE THERAPY FACILITY

CROSS-REFERENCE TO RELATED APPLICATIONS

This application is a continuation-in-part application of U.S. application Ser. No. 11/433,644, filed May 12, 2006, which is incorporated herein by reference in its entirety for all purposes. This application also claims priority to U.S. Provisional Application Ser. No. 61/227,211 filed on Jul. 21, 2009, which is incorporated herein by reference in its entirety for all purposes.

This invention was made with Government support under contract number DE-AC02-98CH10886, awarded by the U.S. Department of Energy. The Government has certain rights in the invention.

BACKGROUND OF THE INVENTION

The present invention relates generally to a medical cancer therapy facility and, more particularly, to a medical particle delivery system having a compact gantry design.

It has been known in the art to use a particle accelerator, such as a synchrotron, and a gantry arrangement to deliver a beam of particles, such as protons, from a single source to one of a plurality of patient treatment stations for cancer therapy. In such systems, the cancerous tumor will be hit and destroyed by particles in a precise way with a localized energy deposition. Thus, the number of ion interactions on the way to the tumor through the healthy body cells is dramatically smaller than by any other radiation method. A position of the center of the tumor inside the body defines a value of the particle energy. The transverse beam raster is defined by the transverse size of the tumor with respect to the beam, while the width of the tumor defines the beam energy range. The energy deposition is localized around the "Brag" peak of the "implanted particles" and remaining energy is lost due to particle interaction with the tumor cells.

Such cancer treatment facilities are widely known throughout the world. For example, U.S. Pat. No. 4,870,287 to Cole et al. discloses a multi-station proton beam therapy system for selectively generating and transporting proton beams from a single proton source and accelerator to one of a plurality of patient treatment stations each having a rotatable gantry for delivering the proton beams at different angles to the patients. A duoplasmatron ion source generates the protons which are then injected into an accelerator at 1.7 MeV. The accelerator is a synchrotron containing ring dipoles, zero-gradient dipoles with edge focusing, vertical trim dipoles, horizontal trim dipoles, trim quadrupoles and extraction Lambertson magnets.

The beam delivery portion of the Cole et al. system includes a switchyard and gantry arrangement. The switchyard utilizes switching magnets that selectively direct the proton beam to the desired patient treatment station. Each patient treatment station includes a gantry having an arrangement of bending dipole magnets and focusing quadrupole magnets. The gantry is fully rotatable about a given axis so that the proton beam may be delivered at any desired angle to the patient.

The gantry of typical particle beam cancer therapy systems accepts a particle beam of a required energy from the accelerator and projects it with a high precision toward a cancerous tumor within a patient. The beam from the isocentric gantry must be angularly adjustable so that the beam can be directed into the patient from above and all sides. Because of these requirements, the gantry of a conventional particle beam cancer therapy facility is typically the most expensive piece of equipment of the treatment facility and its magnets are generally very large and heavy.

For example, the proton-carbon medical therapy facility described by R. Fuchs and P. Emde in "The Heavy Ion Gantry of the HICAT Facility" includes an isocentric gantry system for delivery of protons, Helium, Carbon and Oxygen ions to patients. The gantry system has a total weight of 630 tons and the required beam line elements for transporting and delivering fully stripped Carbon and Oxygen ions with 430 MeV/nucleon kinetic energy have a total weight of 135 tons. The rotating part of the isocentric gantry system weighs about 570 tons due to its role to safely transport and precisely delivers ions to the patients.

Advances in particle accelerator design have resulted in accelerators utilizing smaller and less complex magnet arrangements. For example, a nonscaling fixed field alternating gradient (FFAG) accelerator has recently been developed which utilizes fixed field magnets, as opposed to much larger and more complex variable magnetic field coil magnets. Such advances, however, have heretofore not been applied to the gantry design of typical cancer therapy facilities.

Accordingly, it would be desirable to improve upon the prior art medical cancer therapy facilities by providing a simpler, less expensive and more compact gantry design utilizing some of the advances made in the field of particle accelerators.

SUMMARY OF THE INVENTION

The present invention is a particle therapy gantry for delivering a particle beam to a patient. The gantry generally includes a beam tube having a curvature defining a particle beam path and a plurality of fixed field magnets sequentially arranged along the beam tube for guiding the particle beam along the particle path.

In a preferred embodiment, each of the fixed field magnets is a combined function magnet performing a first function of bending the particle beam along the particle path and a second function of focusing or defocusing the particle beam. Also, the magnets are preferably arranged in triplets, wherein each triplet has two focusing magnets and one defocusing magnet disposed between the focusing magnets. The focusing magnets perform the combined function of bending the particle beam and focusing the particle beam and the defocusing magnet performs the combined function of bending the particle beam and defocusing the particle beam. The defocusing magnets are preferably positive bending magnets for bending the particle beam along an arc defined by a positive center of curvature and the focusing magnets are preferably negative bending magnets for bending the particle beam along an arc defined by a negative center of curvature, wherein the positive and negative centers of curvature are oriented on opposite sides of the beam pipe.

In one embodiment, the fixed field magnets are permanent magnets including a ferromagnetic core having a curvature defined by a center of curvature and forming a beam tube receiving cavity having the beam tube supported therein. The core is shaped to provide a magnetic field in the beam tube which grows stronger in a direction toward the core center of curvature. In an alternative embodiment, the fixed field magnets include superconducting coils adjacent the beam tube for providing the combined function.

In either case, the beam tube of the gantry preferably includes a particle beam entry point, a transition point, a particle beam exit point, a first curved particle beam path arc length extending between the entry point and the transition point and a second curved particle beam path arc length extending between the transition point and the exit point. The first arc length bends about ninety degrees and the second arc length bends about one hundred eighty degrees in a direction opposite the first arc length. Two half-triplets are preferably disposed in juxtaposed orientation at the beam tube transition point and a half-triplet is preferably disposed at each of the beam tube entry point and the beam tube exit point. Each of the half-triplets includes a defocusing magnet and a focusing magnet.

The present invention further involves a method for delivering a particle beam to a patient through a gantry. The method generally includes the steps of bending the particle beam with a plurality of fixed field magnets sequentially arranged along a beam tube of the gantry, wherein the particle beam travels in the beam tube, and alternately focusing and defocusing the particle beam traveling in the beam tube with alternately arranged combined function focusing and defocusing fixed field magnets.

In a preferred embodiment, the combined function fixed field magnets are arranged in triplets, wherein each triplet includes two focusing magnets and one defocusing magnet disposed between the focusing magnets. The focusing magnets perform the combined function of bending the particle beam and focusing the particle beam and the defocusing magnet performs the combined function of bending the particle beam and defocusing the particle beam. The defocusing magnets are preferably positive bending magnets for bending the particle beam along an arc defined by a positive center of curvature and the focusing magnets are preferably negative bending magnets for bending the particle beam along an arc defined by a negative center of curvature, wherein the positive and negative centers of curvature are oriented on opposite sides of the beam pipe.

The gantry of the present invention may be utilized in a medical particle beam therapy system having a source of particles, a particle accelerator, an injector for transporting particles from the source to the accelerator, one or more patient treatment stations including rotatable gantries of the present invention for delivering a particle beam to a patient and a beam transport system for transporting the accelerated beam from the accelerator to the patient treatment station.

In an alternative embodiment, the combined function magnets are replaced by separate function, fixed-field permanent magnets. In this embodiment, the fixed-field permanent magnets are arranged in a series of unit cells, wherein each cell includes two bending dipole magnets, a focusing quadrupole magnet and two defocusing quadrupole magnets. The bending dipole magnets perform the function of bending the particle beam along the particle beam path, the focusing quadrupole magnet performs the function of focusing the particle beam along the particle beam path and the defocusing quadrupole magnets perform the function of defocusing the particle beam along the particle beam path.

The bending dipole magnets are preferably separated by the defocusing quadrupole magnet and flanked by the focusing quadrupole magnet. In this manner, the unit cell is symmetric with respect to the longitudinal center of the defocusing quadrupole magnet.

The defocusing quadrupole magnet has a linear horizontal defocusing gradient, whereby particles of the beam path tend to disperse along a plane defined by a radius of curvature of the beam tube, but tend to concentrate with respect to a plane perpendicular to the radius of curvature. Conversely, the two focusing quadrupole magnets have a linear horizontal focusing gradient, whereby particles tend to concentrate along the plane defined by the radius of curvature of the beam tube, but tend to disperse along the plane perpendicular to the plane defined by the radius of curvature of the beam tube.

Each of the fixed field permanent magnets preferably include a plurality of ferromagnetic segments radially arranged around a magnet center, wherein each segment has a fixed magnetic field oriented in a predetermined direction. The bending dipole magnet can include eight of these segments arranged to produce a combined dipole magnetic field across the magnet center. Each of the quadrupole magnets can include sixteen of these segments arranged to produce a quadrupole magnetic field across the magnet center.

The beam tube has a radial center line, and each of the defocusing quadrupole magnets is rotated about the beam tube center line to produce a quadrupole magnetic field that flows from a plane perpendicular to a plane defined by a radius of curvature of the beam tube to the plane defined by the radius of curvature of the beam tube. Each of the focusing quadrupole magnets is rotated about the beam tube center ninety degrees with respect to the defocusing quadrupole magnets to produce a quadrupole magnetic field that flows from the plane defined by the radius of curvature of the beam tube to the plane perpendicular to the plane defined by the radius of curvature of the beam tube.

According to a method of the alternative embodiment of the present invention, the particle beam is bent with a plurality of fixed field permanent magnets sequentially arranged along a beam tube of the gantry, the particle beam is alternately focused and defocused with alternately arranged focusing and defocusing fixed field permanent magnets and the particle beam is delivered from the gantry to a patient, wherein the beam is strongly focused in both the horizontal and vertical planes.

This alternative embodiment of the gantry can also be utilized in a medical particle beam therapy system as described above with respect to the combined function magnets. In this case, the system includes a source of particles, an accelerator for accelerating the particles as a particle beam, an injector for transporting particles from the source to the accelerator, a patient treatment station including a rotatable gantry for delivering a particle beam to a patient and a beam transport system for transporting the accelerated beam from the accelerator to the patient treatment station. The gantry in this case includes a beam tube having a curvature defining a particle beam path and a plurality of fixed field permanent magnets sequentially arranged along the beam tube for guiding the particle beam along the particle path.

The gantry may include a particle beam entry point, a transition point, a particle beam exit point, a first curved particle beam path arc length extending between the entry point and the transition point and a second curved particle beam path arc length extending between the transition point and the exit point. The first arc length bends about ninety degrees and the second arc length bends about one hundred eighty degrees in a direction opposite the first arc length. In this case, the fixed field magnets include two half-cells disposed in juxtaposed orientation at the beam tube transition point, a half-cell disposed at the beam tube entry point and a half-cell disposed at the beam tube exit point. Each of the half-cells includes a bending dipole magnet, a defocusing quadrupole magnet and a focusing quadrupole magnet.

The preferred embodiments of the particle beam gantry of the present invention, as well as other objects, features and advantages of this invention will be apparent from the following detailed description, which is to be read in conjunction with the accompanying drawings. The scope of the invention will be pointed out in the claims.

DETAILED DESCRIPTION OF THE PREFERRED EMBODIMENTS

Figure 1:
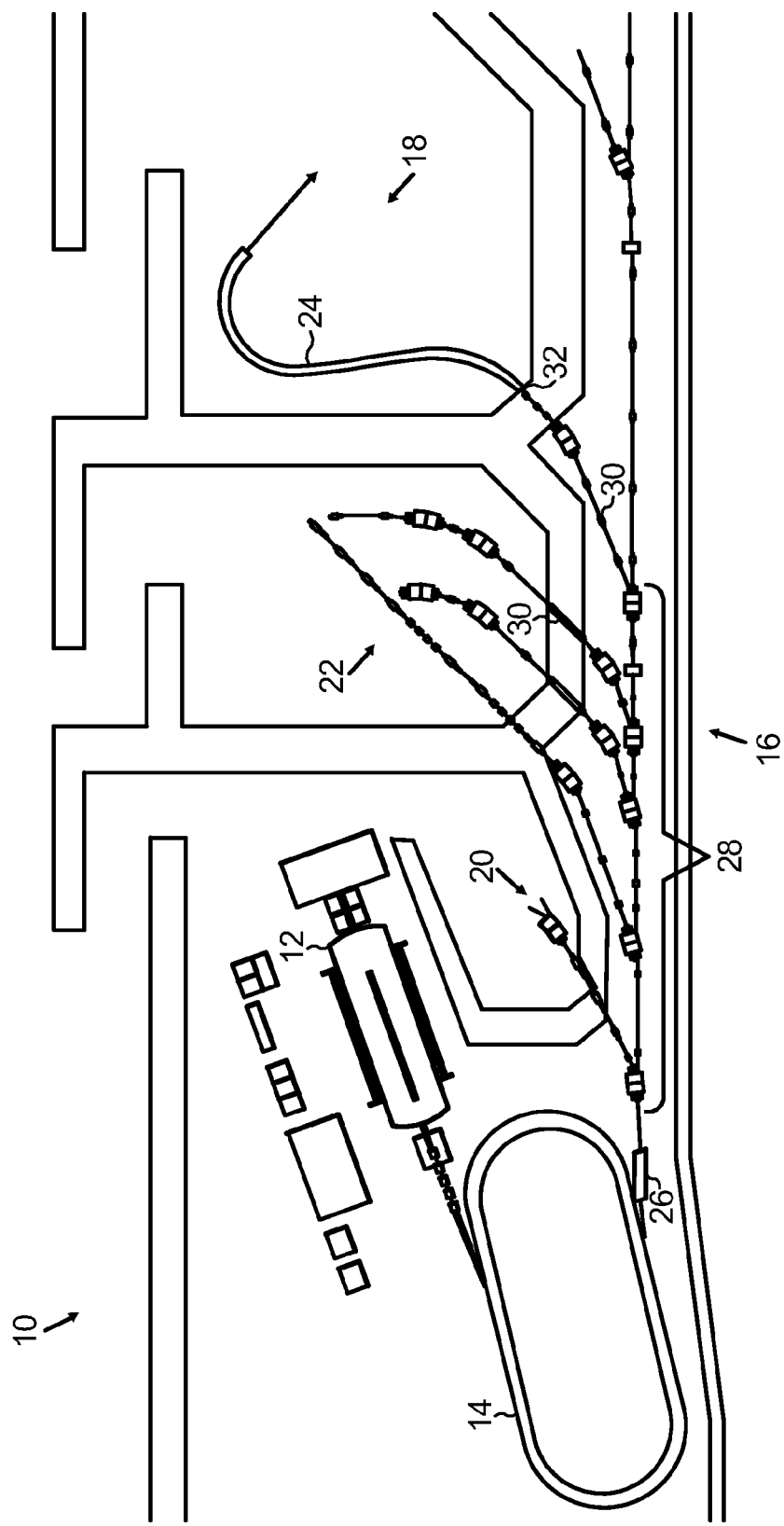
FIG. 1 is a top plan view of a typical medical particle delivery therapy facility.

FIG. 1 shows a typical medical particle delivery therapy facility 10. The facility 10 generally includes an injector 12, a particle accelerator 14, and a beam delivery network 16 including a rotatable gantry treatment room 18 for delivering a beam to a patient. The beam delivery network 16 may also be designed to divert independent beams to various other applications as desired. For example, the beam delivery network 16 may be designed to deliver a beam to a beam research room 20 and a fixed beam treatment room 22. The research room 20 may be provided for research and calibration purposes, with an entrance separate from the patient areas, while the fixed beam treatment room 22 may include separate beam lines for such therapeutic applications, such as eye treatments.

The beam injector module 12 can be a conventional LINAC or a tandem Van de Graaf injector with an injection kicker, which completes the task of particle injection into the accelerator 14. In the case of proton particles, the injector typically provides proton beam pulses at 30 Hz with a pulse width varying between 25 and 100 nanoseconds at a delivered energy of 7 MeV.

The particle accelerator 14 can be a synchrotron, cyclotron or some other conventional design known in the prior art. The accelerator 14 accelerates particles to a desired energy level for extraction and delivery to the patient treatment rooms 18 and 22. Variation of the extraction energy is achieved by adjusting, for example, an RF frequency within the accelerator 14. Again for proton particles, extraction typically occurs when the kinetic energy of the particles is in the range 60 to 250 MeV.

The beam delivery network 16 connects the accelerator 14 to the treatment rooms 18 and 22 and the beam research room 20. The network 16 generally includes an extraction line 26, a switchyard 28 and a plurality of beam transport lines 30. The switchyard 28 is typically an arrangement of switching magnets for diverting the particle beam to a desired beam line 30. The beam transport lines 30 take the particle beam from the switchyard 28 to the different treatment rooms of the facility.

Figure 2:
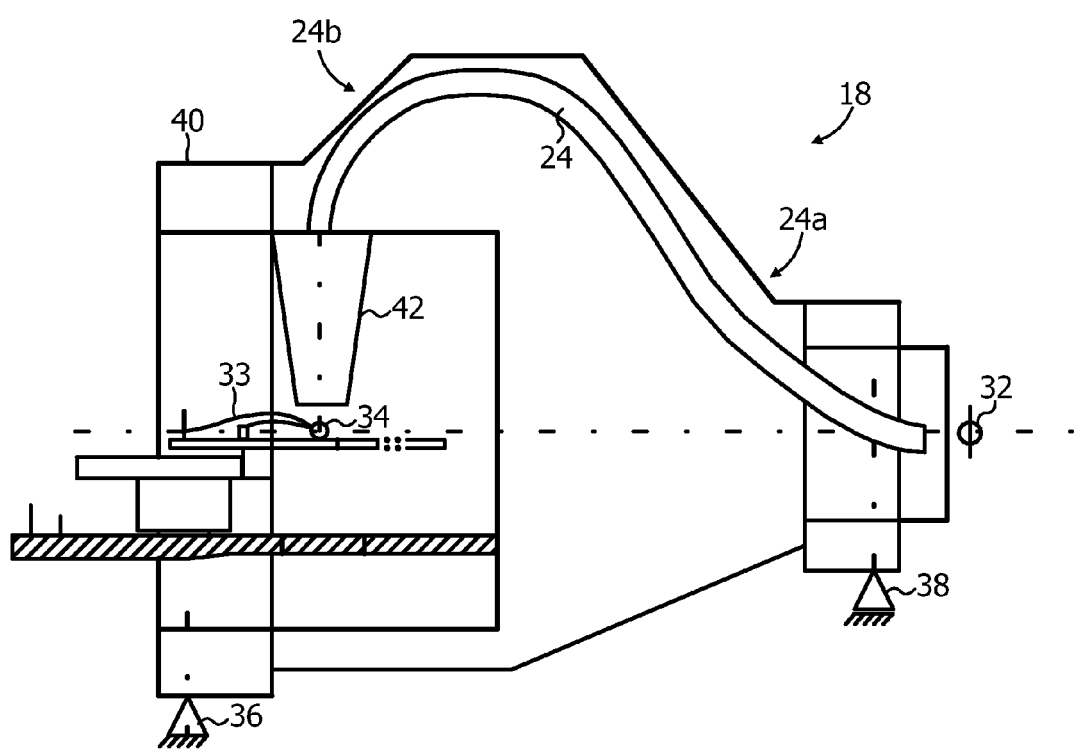
FIG. 2 is a side view of the arrangement of the gantry treatment room of the medical facility shown in FIG. 1.

Referring additionally to FIG. 2, the rotatable gantry treatment room 18 includes a rotating gantry 24, which is rotatable by plus or minus 200 degrees from the vertical about a point of rotation 32 to deliver a particle beam to a patient 33 at a gantry iso-center 34. The gantry system accepts particles already accelerated to required energy. The first part 24a of the gantry bends particles within a quarter of a circle for 90 degrees. The second part 24b of the gantry bends the particles in a half of a circle and brings the particles straight towards the required direction 34.

The gantry 24 is constructed as a three-dimensional structure supported on the treatment room side by a bearing 36 and, on the beam inlet side, by a bearing 38. The gantry 24 is further preferably balanced around its rotation axis. Gantry movement can be realized by a gear motor/gear ring drive 40 that allows high precision positioning. Each gantry 24 is preferably controlled by means of an individual independent computer unit that ensures mutual braking of the main drive units, soft start and soft deceleration functions, control of the auxiliary drive units for the treatment room, and supervision of the limit switches. The gantry 24 further includes a nozzle 42 for delivering the particle beam to the patient 33.

Figure 3:
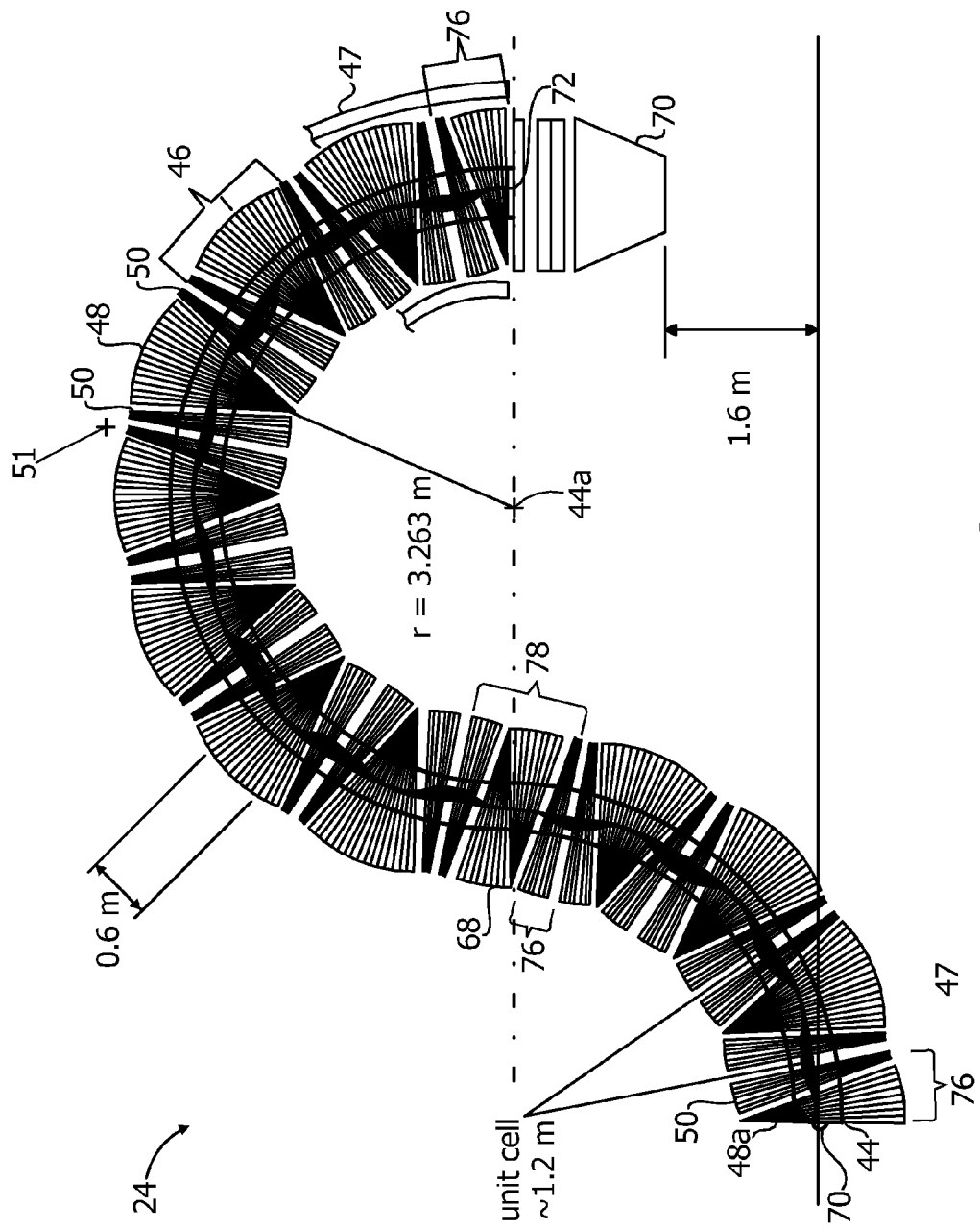
FIG. 3 is a cross-sectional view of the gantry according to the present invention.

Referring now to FIG. 3, the optical components of the gantry 24 according to the present invention are shown. The gantry 24 generally includes a hook-shaped beam pipe 44 and a series of identical fixed-field magnet triplets 46 arranged in sequence around the beam pipe. The beam pipe 44 can be provided as a continuous pipe, or it can be assembled from a plurality of beam pipe segments welded or otherwise fastened together in a conventional manner. The beam pipe 44 and the magnet triplets 46 are enclosed in a gantry housing 47.

Figure 4:
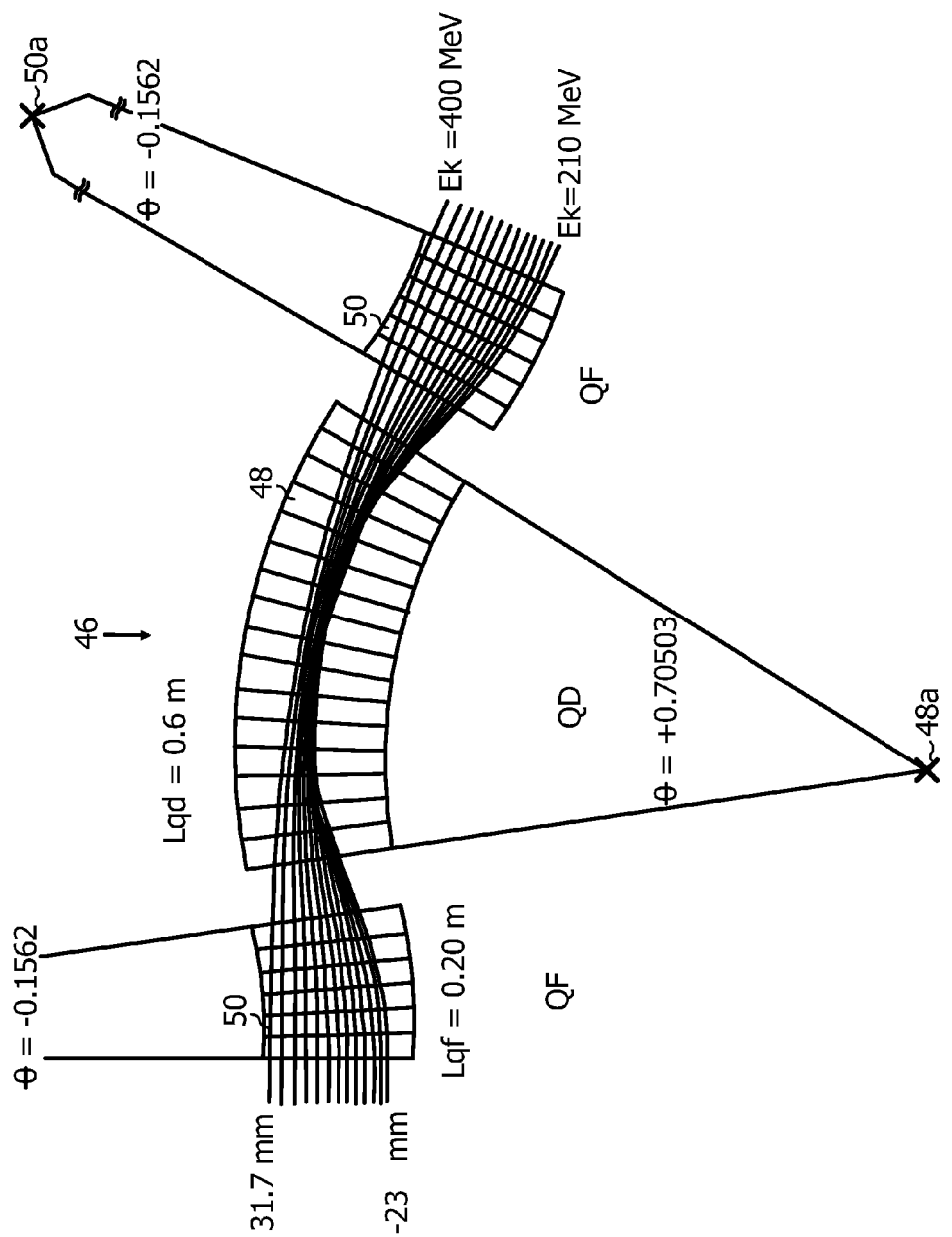
FIG. 4 is a graphical representation of one of the magnet triplets forming the gantry of the present invention.
Figure 5:
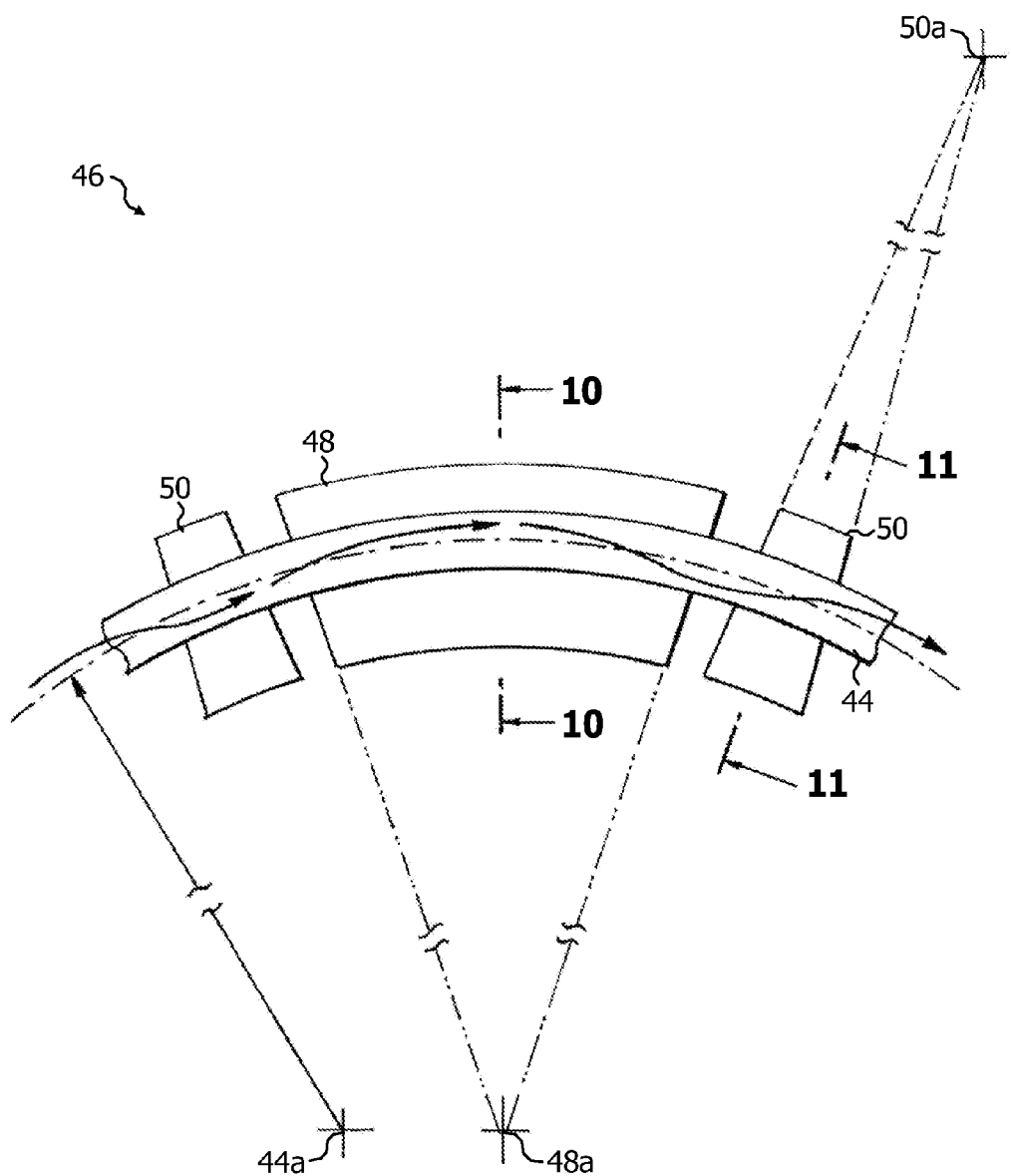
FIG. 5 is another a graphical representation of one of the magnet triplets forming the gantry of the present invention.
Figure 6:
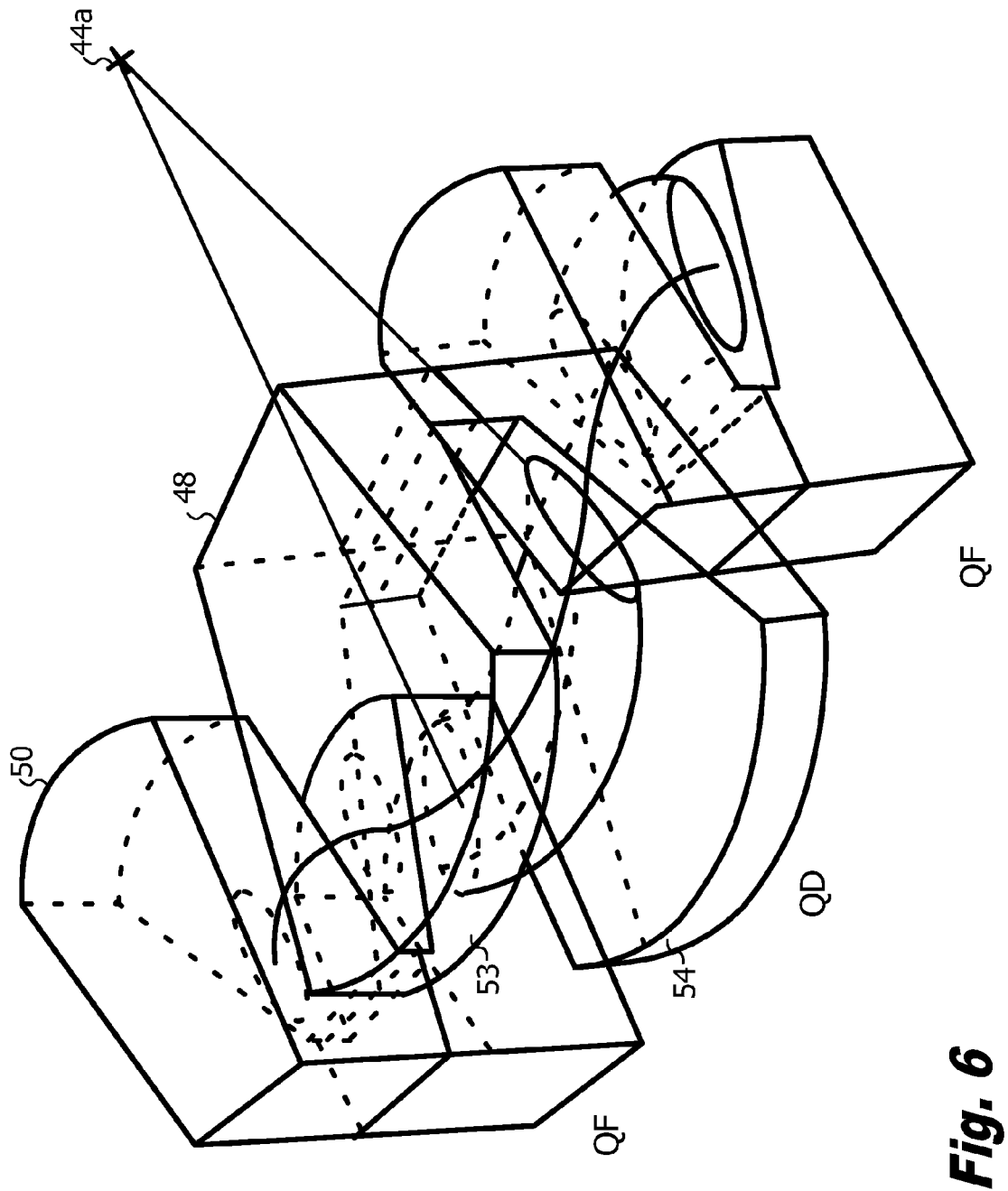
FIG. 6 is an isometric view of one of the magnet triplets forming the gantry of the present invention.

Referring additionally to FIGS. 4-6, the magnet triplet 46 is considered the "unit cell" and contains a relatively long combined function bending/defocusing magnet (QD) 48 flanked by a pair of shorter combined function bending/focusing magnets (QF) 50. The cell 46 is symmetric with respect to the center of the defocusing magnet 48.

Thus, the gantry 24 is made of densely packed identical "triplet" cells 46. Three combined function magnets make a cell. The central magnet 48 produces major bending and has a linear horizontal defocusing gradient. Two smaller identical but opposite bending magnets 50 are placed on both sides of the major bending magnet 48. They have a linear focusing gradient. Each of the combined function magnets 48 and 50 performs two functions. The first function is to bend the particle beam along an orbital path, while the second function is to focus or defocus the particle beam as it travels around the path.

Figure 7:
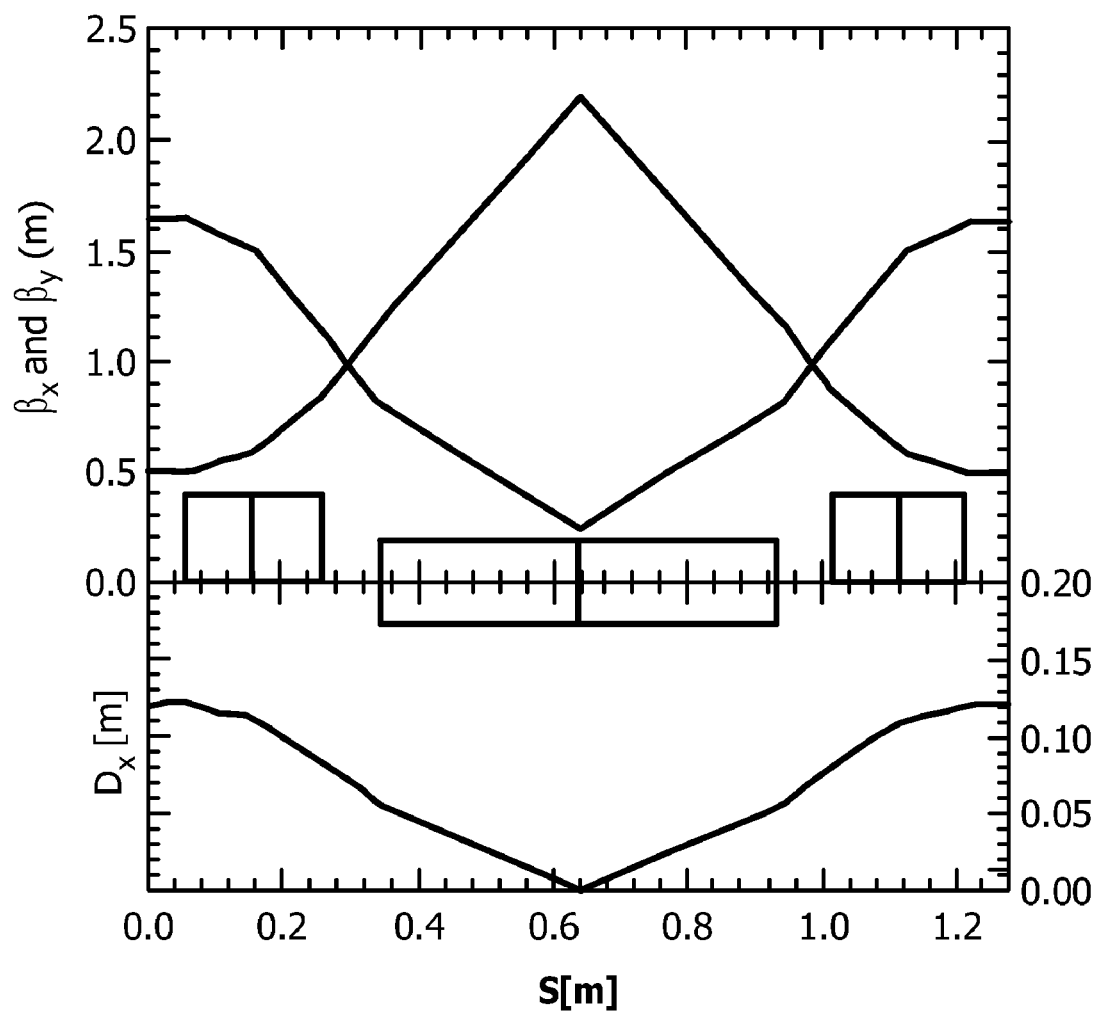
FIG. 7 is a graph showing the horizontal and vertical betatron functions and the dispersion function of a magnet triplet at the reference momentum.
Figure 8:
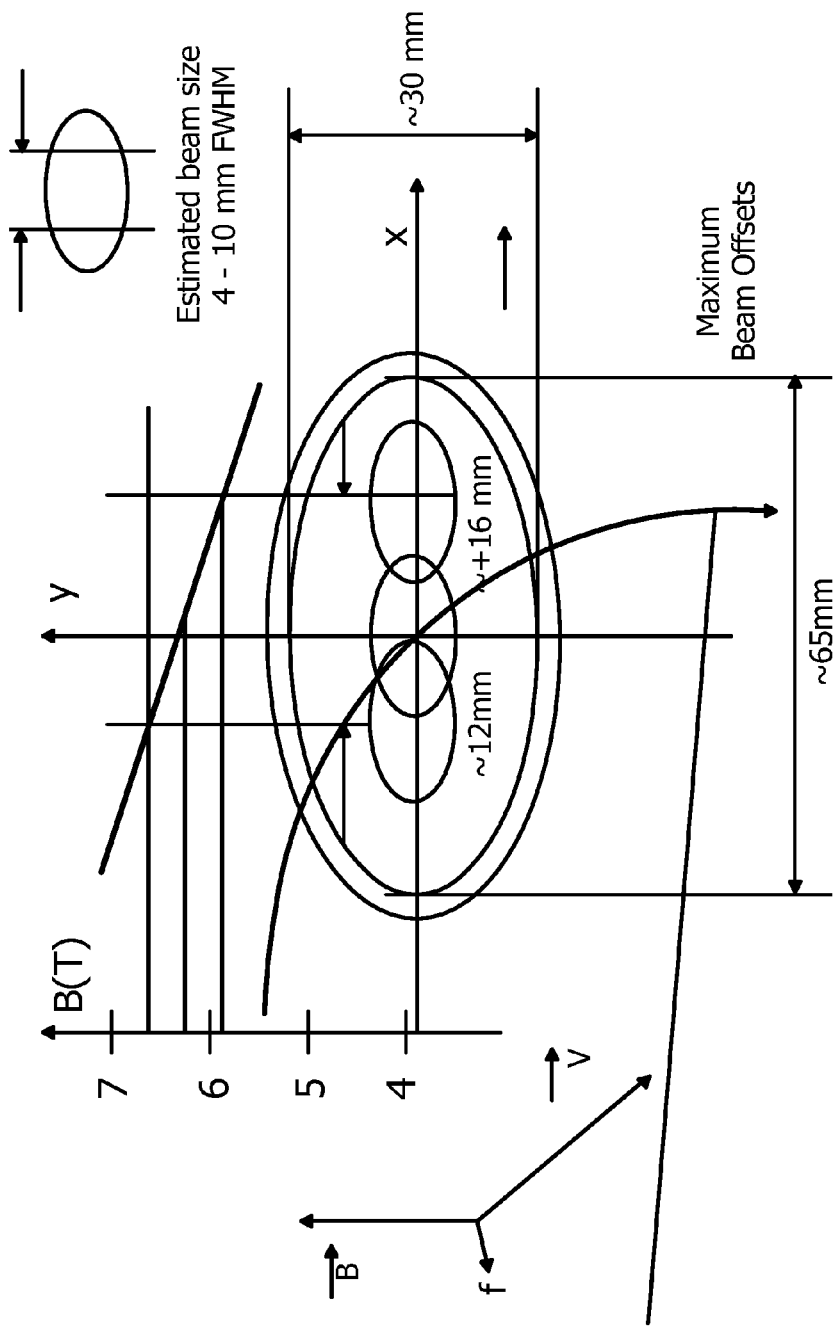
FIG. 8 is a graph showing the minimum required aperture for a combined function magnet with a defocusing gradient.
Figure 9:
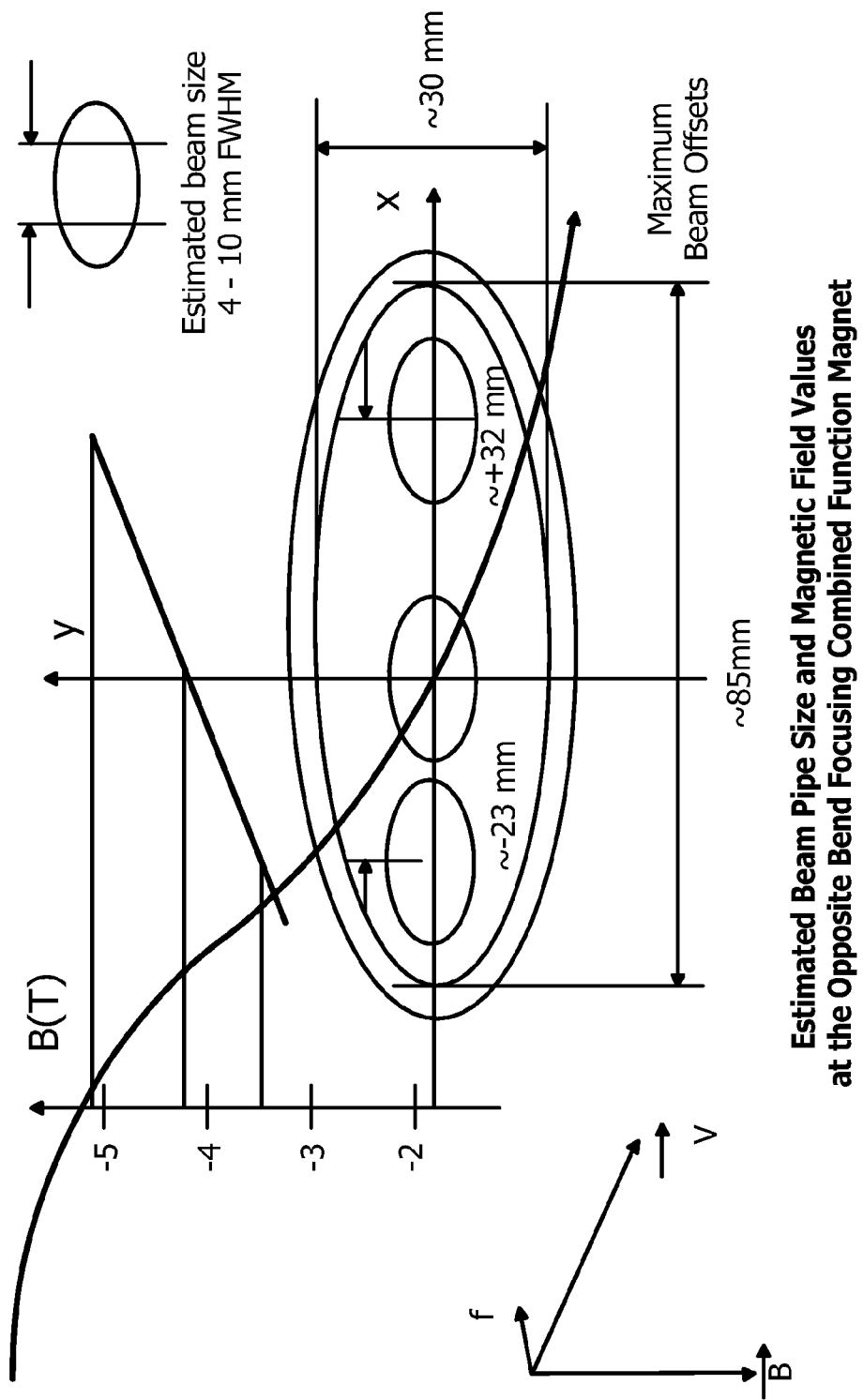
FIG. 9 is a graph showing the minimum required aperture for a combined function magnet with an opposite bend and focusing field.

The defocusing magnet (QD) 48 has a strong central field and a negative gradient (horizontally defocusing) at the center, while the focusing magnets (QF) 50 have a positive gradient (horizontally focusing). Both magnets 48 and 50 are fixed field dipole-type magnets using a very strong focusing and small dispersion function. The horizontal and vertical betatron functions $\beta x$ and $\beta y$ and the dispersion function in the basic cell 46, at the reference momentum, are shown in FIG. 7. The minimum required aperture for the two combined function magnets major bend with the defocusing gradient and the opposite bend with the focusing field are presented in FIGS. 8 and 9, respectively.

Thus, the QD and QF magnets 48 and 50 are arranged in a non-scaling, fixed field alternating gradient (FFAG) configuration. Such FFAG configurations have been used before in particle accelerators, but have heretofore never been proposed in a therapeutic particle delivery gantry of a medical facility.

Also, both types of magnets 48 and 50 are somewhat arc-shaped or wedge-shaped when viewed in a direction perpendicular to the path of the beam pipe 44. Thus, each magnet 48 and 50 is defined by an axis 48a and 50a, which may represent the center of curvature in the case of an arc-shaped magnet, or an intersection point of the two outside faces in the case of a wedge-shaped magnet.

In either case, each defocusing magnet (QD) 48 of each magnet triplet 46 is arranged along the beam pipe 44 so that its axis 48a falls on the same side of the beam pipe 44 as the beam pipe's center of curvature 44a. Conversely, each flanking pair of focusing (QF) magnets 50 of each magnet triplet is arranged along the beam pipe 44 so that their axes 50a falls on the opposite side of the beam pipe 44 as the beam pipe's center of curvature 44a. In this manner, each defocusing magnet (QD) 48 can be termed a "positive bending" magnet, wherein the shape and arrangement of this magnet bends the particles passing therethrough in a path generally matching the curvature of the beam pipe, as shown in FIGS. 3-6. Each focusing magnet (QD) 50, on the other hand, can be termed a "negative bending" magnet, wherein the shape and arrangement of these magnets bend the particles passing therethrough in a path generally opposite to the curvature of the beam pipe. It has been found that such alternating arrangement of positive and negative bending magnets results in a particle beam having a reduced dispersion.

Figure 10:
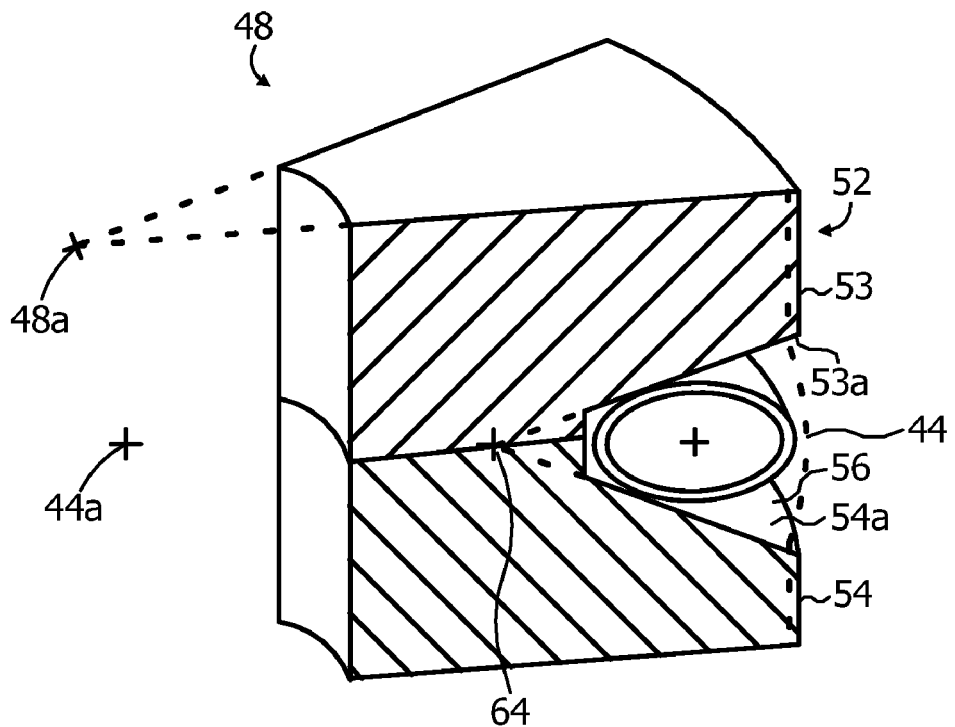
FIG. 10 is a cross-sectional view of the combined function bending/defocusing magnet shown in FIG. 5, taken along line 10-10.

Referring now to FIG. 10, each defocusing magnet (QD) 48 includes a ferromagnetic core 52 made up of an upper 53 and a lower half 54 forming a dipole magnet. The upper 53 and lower halves 54 are identical in cross-section and can be solid ferromagnetic masses, as shown in FIG. 10, or they can be made from a series of stacked laminates. In either case, the upper core half 53 includes an angled face 53a and the lower core half includes an angled face 54a. The angled faces 53a and 54a of the upper and lower core halves 53 and 54 face each other and form a beam pipe receiving cavity 56 when the core halves are assembled together to form the magnet core 52.

Figure 11:
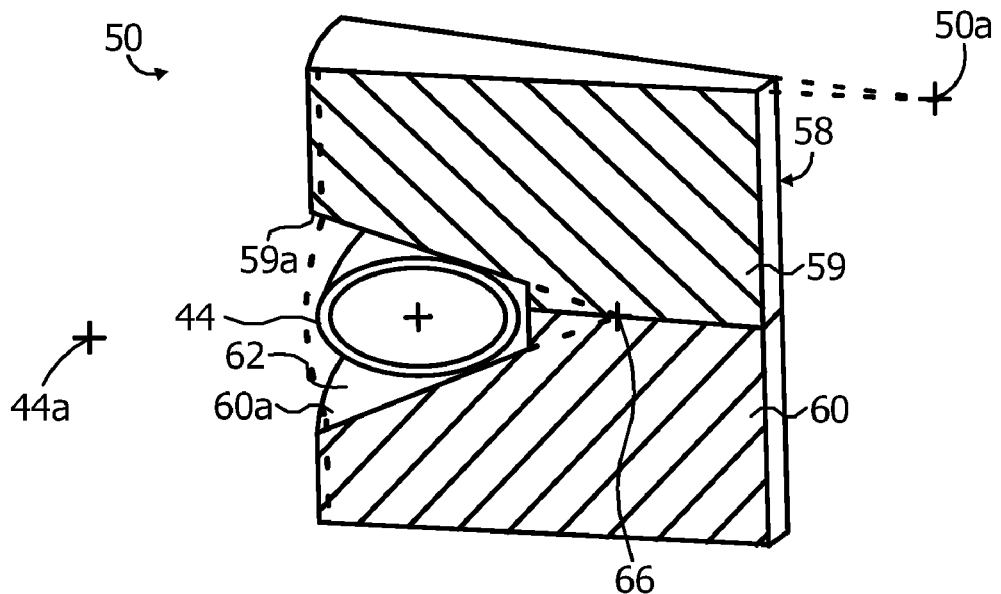
FIG. 11 is a cross-sectional view of the combined function bending/focusing magnet shown in FIG. 5, taken along line 11-11.

Referring to FIG. 11, each focusing magnet (QF) 50 is similarly constructed. Specifically, each focusing magnet 50 includes a ferromagnetic core 58 made up of an upper 59 and a lower half 60 forming a dipole magnet. Again, the upper 59 and lower halves 60 can be solid ferromagnetic masses or they can be made from a series of stacked laminates 55. Also, the upper core half 59 includes an angled face 59a and the lower core half includes an angled face 60a. The angled faces 59a and 60a of the upper and lower core halves 59 and 60 face each other and form a beam pipe receiving cavity 62 when the core halves are assembled together to form the magnet core 58.

As mentioned above, each magnet 48 and 50 is a combined function arc magnet combining the functions of bending the particle beam and focusing or defocusing the particle beam. The bending function is achieved by the curvature of the magnet, while the focusing or defocusing function is achieved by the arrangement of the magnet cores 52, 58.

In particular, the upper 53 and the lower 54 halves of the defocusing magnet core 52 are arranged together respectively above and below the beam pipe 44 so as to provide a magnetic field in the beam pipe which grows stronger in a direction toward the center of curvature 48a of the core, as shown in FIG. 10, whereas the upper and the lower halves 59 and 60 of a focusing magnet core 58 are arranged together respectively above and below the beam pipe so as to provide a magnetic field in the beam pipe which grows weaker in a direction toward the center of curvature of the defocusing core 48a, but which grows stronger in a direction toward the center of curvature 50a of its own core.

Thus, in a defocusing combined function magnet 48, as shown in FIG. 10, a proton, or other particle, in the beam pipe 44 radially further from the core center of curvature 48a and the beam pipe center of curvature 44a (to the right in FIG. 10) is subject to a weaker magnetic field and bends less, while a proton, or other particle, closer to the beam pipe center of curvature (to the left in FIG. 10) sees a stronger magnetic field and bends more. This results in a more dispersed horizontal concentration of protons, but a denser vertical concentration, in the beam pipe just downstream of a defocusing combined function magnet.

Conversely, in a focusing combined function magnet 50, as shown in FIG. 11, a proton, or other particle, in the beam pipe 44 radially further from the beam pipe center of curvature 44a, or closer to the core center of curvature 50a, (to the right in FIG. 11) is subject to a stronger magnetic field and bends more, while a proton closer to the beam pipe center of curvature, or away from the core center of curvature, (to the left in FIG. 11) sees a weaker magnetic field and bends less. This results in a greater horizontal concentration of particles, but a weaker vertical concentration of particles in the beam pipe just downstream of a focusing combined function magnet.

The above defocusing effect is achieved by orienting the angled surfaces 53a and 54a of the upper and lower core halves 53 and 54 of the defocusing magnet core 52 so that they form an intersection point 64 that falls on the same side of the beam pipe 44 as the beam pipe center of curvature 44a, as shown in FIG. 10. A focusing magnet 50 is formed by orienting the angled surfaces 59a and 60a of the upper and lower core halves 59 and 60 of the focusing magnet core 58 so that they form an intersection point 66 that falls on the side of the beam pipe 44 opposite the beam pipe center of curvature 44a, as shown in FIG. 11. In other words, the angled faces 53a and 54a of a defocusing magnet 48 meet adjacent the inner arc of the beam pipe 44, whereas the angled faces 59a and 60a of a focusing magnet 50 meet adjacent the outer arc of the beam pipe, with respect to the center of curvature 44a of the beam pipe.

Accordingly, not only are the positive and negative bending functions alternately arranged, but also the focusing and defocusing functions of the magnets are alternately arranged. Such alternate arrangement of the positive and negative bending and the focusing and defocusing functions provides to the present invention the feature of net strong particle beam focusing in both horizontal and vertical planes.

At the transition point 68 of the gantry 24, where the beam pipe 44 reverses its curvature, and/or at the beam entry point 70 and/or at the beam exit point 74, modifications of the magnet triplet 46 can be utilized to provide the desired bending and focusing/defocusing functions. For example, a half-triplet 76 consisting of a single negative-bend focusing magnet 50 and a reduced length, positive bend defocusing magnet 48a can be utilized at the beam entry point 76 and/or the beam exit point 72 of the gantry to achieve the desired bend angle and focusing at these points. Similarly, at the beam pipe curvature transition point 68, two half-triplets 76, as described above, can be assembled together in a juxtaposed orientation to form a "straight" magnet triplet 78.

For proton therapy systems, the combined function defocusing magnet 48 and the combined function focusing magnet 50 used in the gantry can be very small permanent magnets, as described above. For example, a suitable magnetic field of about 1.8 T can be achieved using defocusing magnets 48 that measure about 6 cm×8 cm×10 cm. For larger particles, such as carbon, the magnets can utilize high-temperature superconductor tapes (HTS) or superconducting Niobium-Tin coils to achieve the required greater magnetic fields of about 6 T. In either case, the magnets are still fixed-field magnets.

Figure 12:
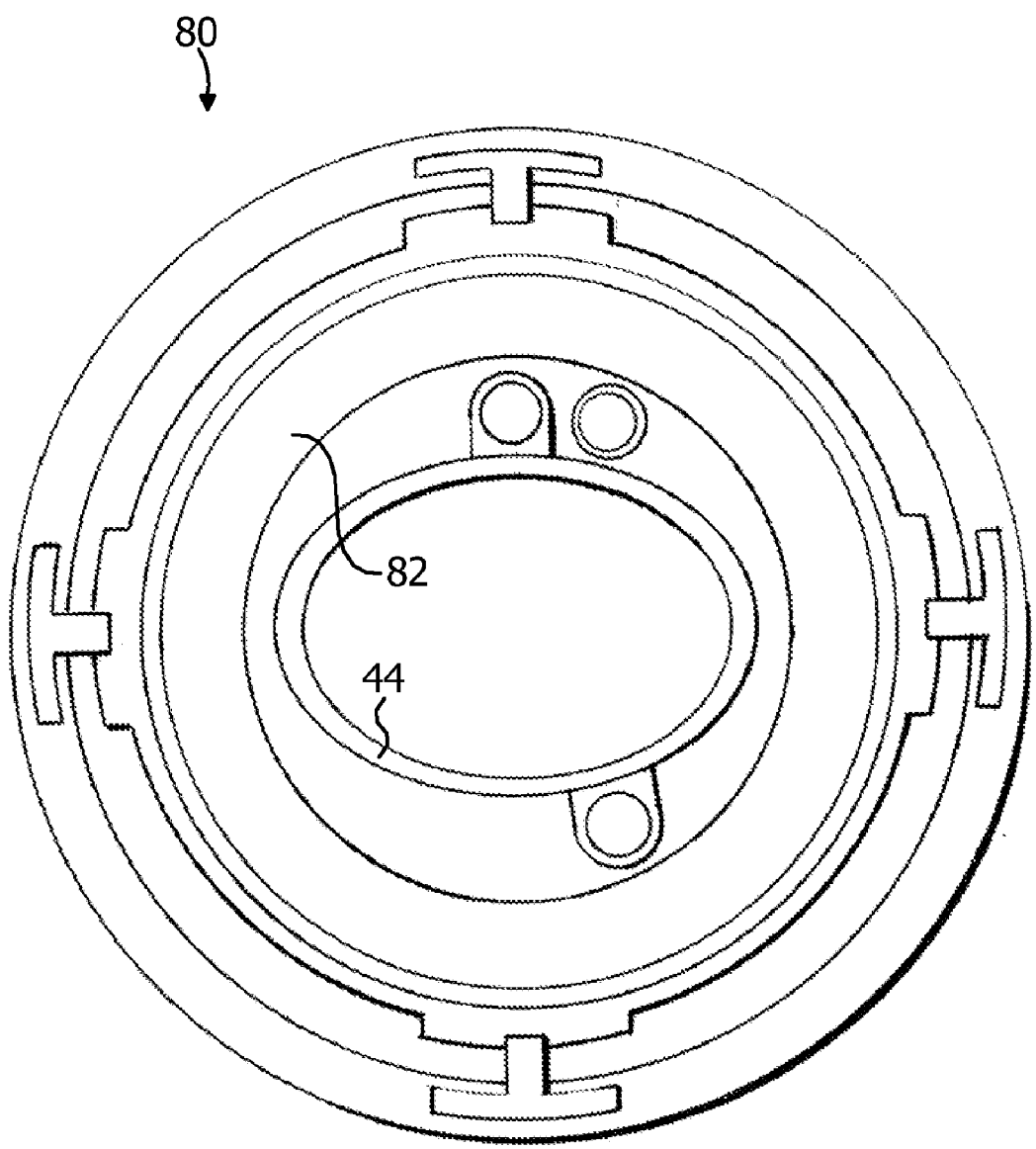
FIG. 12 is a cross-sectional view of a fixed field combined function magnet utilizing superconducting tapes or coils without an iron core.
Figure 13:
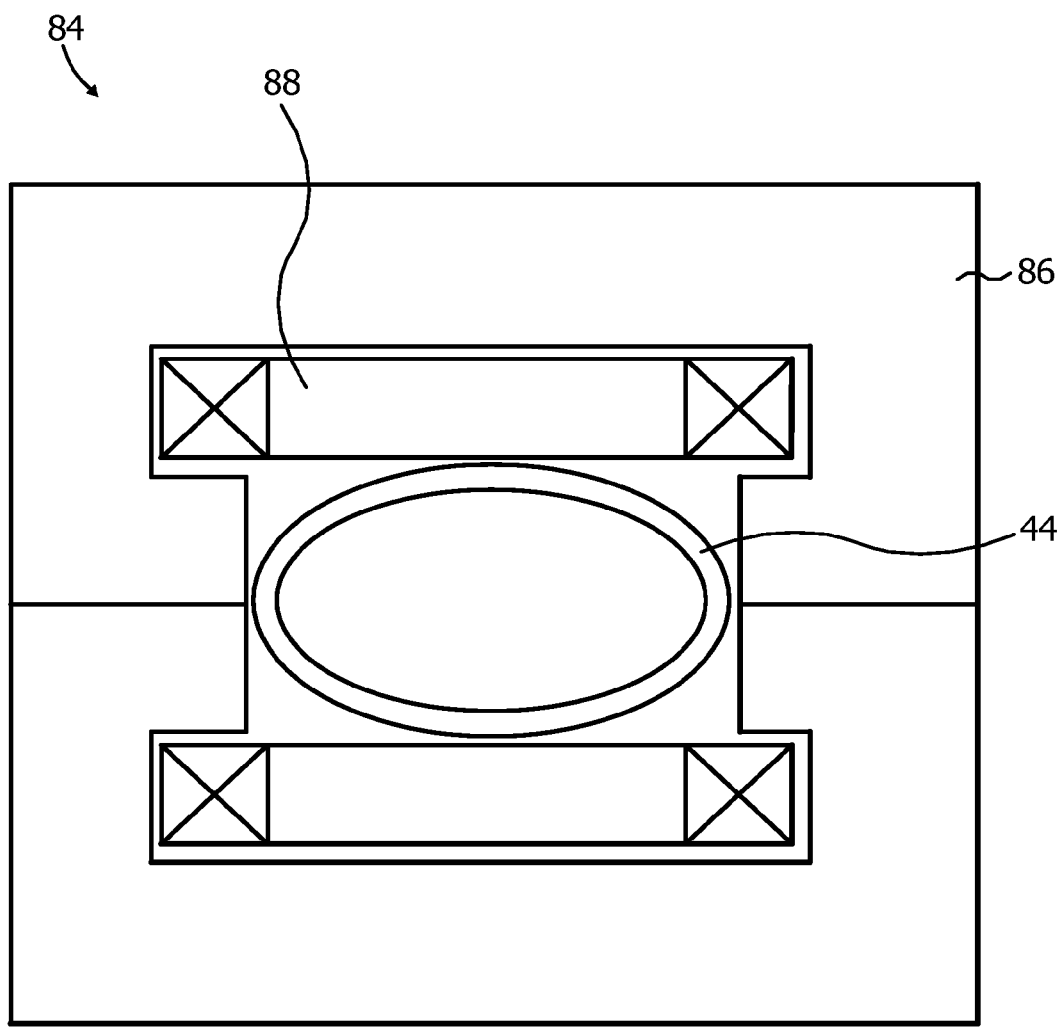
FIG. 13 shows a cross-sectional view of a similar superconducting magnet having a super ferric core and superconducting coils surrounding the beam tube.

FIG. 12 shows a cross-section of a fixed field combined function magnet 80 utilizing high-temperature superconductor tapes (HTS) or superconducting Niobium-Tin coils 82 surrounding the beam tube 44, without an iron core. FIG. 13 shows a cross-section of a similar superconducting magnet 84 having a super ferric core 86 and superconducting coils 88 surrounding the beam tube 44.

As a result of the present invention, the size of the gantry in a particle therapy facility can be dramatically reduced and the control system for a gantry treatment room can be greatly simplified. Specifically, the gantry 24 can be made about 20 meters long, from the rotation point 32 to the iso-center 34, with a height of about 3.2 meters. The gantry 24 preferably has a free space of about 1.6 meters from the last magnet to the isocenter 34.

Thus, the present gantry invention reduces the weight of the gantry system by using a non-scaling Fixed Field Alternating Gradient (FFAG) triplet structure with permanent, superconducting or high-temperature superconducting combined function magnets. This invention allows a very close control of focused ion transport through the beam line with different energies but under the fixed magnetic field. The ions are delivered to the isocentric non-scaling FFAG gantry system at the same entrance position. This invention can achieve presented goals due to a very large momentum acceptance and very strong focusing properties of the non-scaling FFAG structures. The ions with different energies transported through the system arrive at the end of it with small differences in positions (−2.5 up to +3.2 mm) easily adjusted by the raster-scanning focusing part of the gantry.

While use of combined function magnets provides the benefits and superior performance as described above, in an alternative embodiment of the gantry according to the present invention, the combined function magnets described above can be replaced by fixed-field, separate function, permanent magnets. As will be discussed in further detail below, such magnets are simple and inexpensive to manufacture and can be easily assembled and adapted to existing medical facility gantries.

Turning now to FIGS. 14-19, the optical components of the gantry 100 according to the alternative embodiment of the present invention are shown. Again, the gantry 100 generally includes a hook-shaped beam pipe 102 and a series of fixed-field magnets arranged in sequence around the beam pipe. The beam pipe 102 can be provided as a continuous pipe, or it can be assembled from a plurality of beam pipe segments welded or otherwise fastened together in a conventional manner. The beam pipe 102 and the magnets are enclosed in a gantry housing 104.

Figure 14:
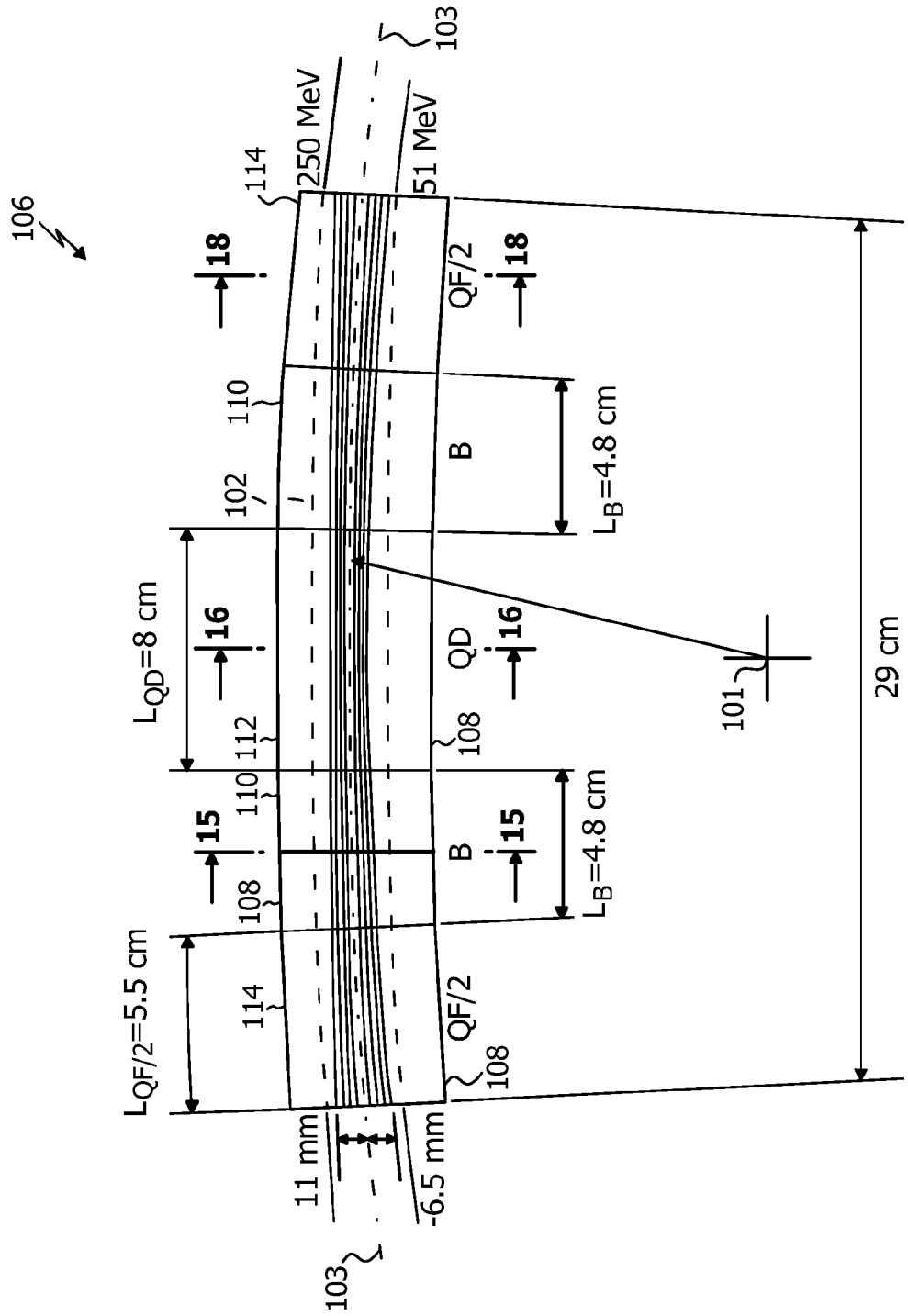
FIG. 14 is a graphical representation of a magnet set forming an alternative embodiment of the gantry of the present invention.

However, in place of the combined function magnet triplets described above, the gantry in this embodiment is made from a series of unit cells 106 having separate function fixed-field permanent magnets 108. In particular, each unit cell 106 includes two bending dipole magnets (B) 110, separated by a defocusing quadrupole magnet (QD) 112 and flanked by two focusing quadrupole magnets (QF/2) 114, as shown in FIG. 14.

As compared to the "combined function" magnets described above, the term "separate function" refers to the fact that each individual magnet 108 in this alternative embodiment of the invention performs only one function. Specifically, each of the two bending dipole magnets (B) 110 only bends the particles along an orbital path around the curvature of the gantry 100, without focusing or defocusing the particles. The defocusing quadrupole magnet (QD) 112 each only defocuses the particles within the beam pipe 102 as they travel around the path, while each of the two focusing quadrupole magnets (QF/2) 114 only focus the particles in the beam pipe.

In this regard, the frame of reference for the terms "defocus" and "focus" is the plane defined by the radius of curvature of the beam pipe 102, sometimes referred to herein as the "horizontal" plane. Thus, the defocusing quadrupole magnet (QD) 112 has a linear horizontal defocusing gradient, wherein particles tend to disperse along the plane defined by the radius of curvature of the beam pipe 102, but tend to concentrate with respect to the plane perpendicular ("vertical") to the radius of curvature, while the two focusing quadrupole magnets (QF/2) 114 have a linear horizontal focusing gradient wherein particles tend to concentrate along the plane defined by the radius of curvature of the beam pipe 102, but tend to disperse along the plane perpendicular ("vertical") to this plane.

The characteristic differences between the combined function triplets described above and the separate function unit cells in this alternative embodiment relate to the fact that, rather than using dipole-type magnets arranged in a specific manner so as to mimic the performance of both a dipole magnet and a quadrupole magnet, the unit cells of this alternative embodiment include true dipole magnets and true quadrupole magnets to separate the functions of bending and focusing/defocusing. In other words, at each point along the beam tube path in the combined function magnet triplet described above, the particles are subject to both bending and focusing/defocusing magnetic forces. In this alternative separate function magnet embodiment, at different points along the beam tube path, the particles are only subject to a bending force or a focusing/defocusing force. Nevertheless, like the combined function magnets described above, the alternate arrangement of the focusing and defocusing functions provides to this alternative embodiment the feature of net strong particle beam focusing in both horizontal and vertical planes.

Referring to FIG. 14, the cell 106 is symmetric with respect to the center of the defocusing quadrupole magnet (QD) 112. The two bending dipole magnets 110 are preferably about 4.8 cm long and are oriented along the beam pipe 102 to bend particles along an arc defined by the beam pipe center of curvature 101. The quadrupole defocusing magnet 112 is preferably about 8 cm long and the two quadrupole focusing magnets 114 are each about 5.5 cm long. As a result, the length of the unit cell 106 is about 29 cm long.

Figure 19:
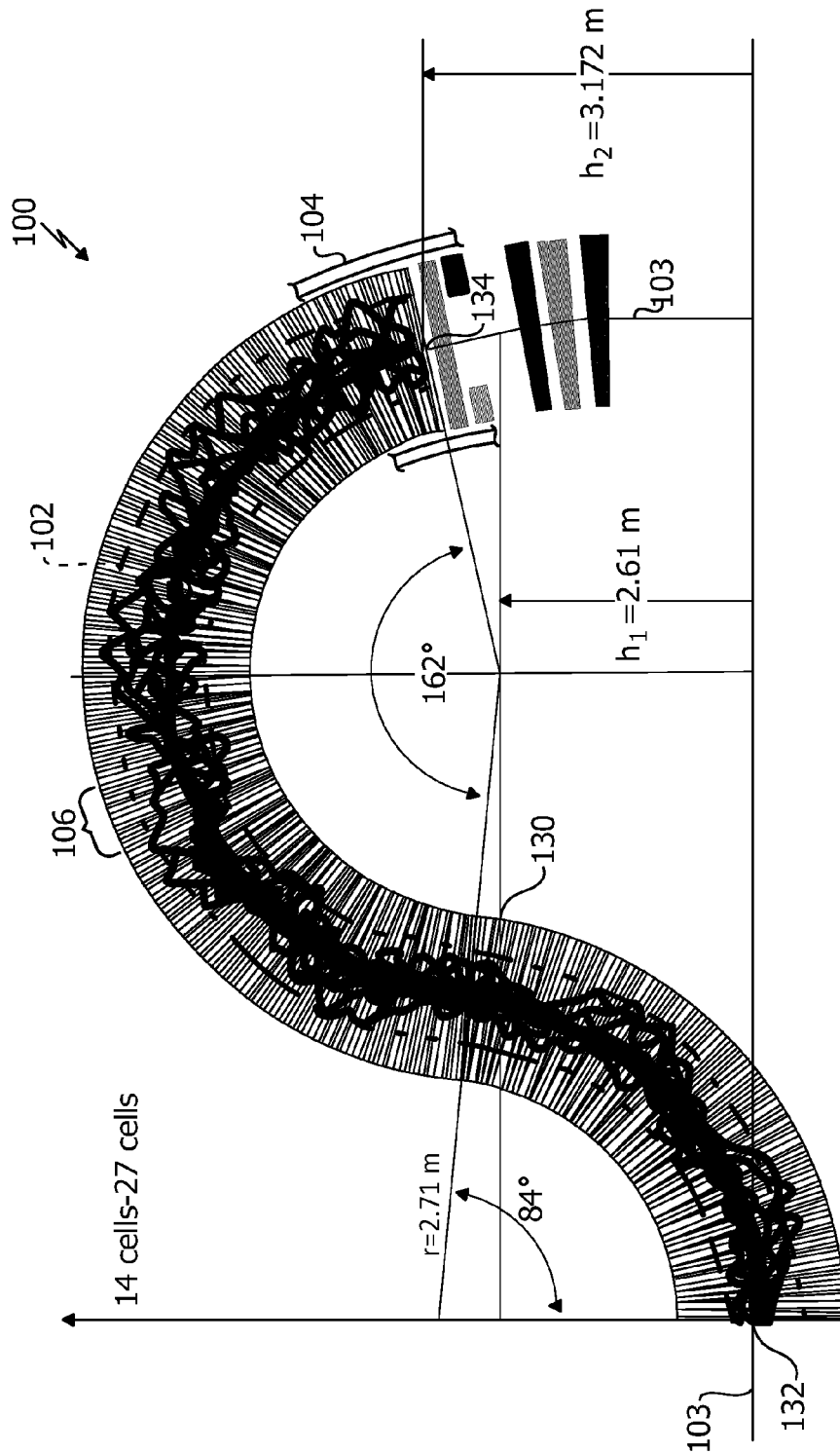
FIG. 19 is a cross-sectional view of the alternative embodiment of the gantry according to the present invention.

Thus, the gantry 100 is made of densely packed identical cells 106 arranged around the curvature of the beam pipe as shown in FIG. 19. In an exemplary embodiment twenty-seven cells make up the 180 degree exit portion of the gantry and fourteen cells make up the 90 degree entry portion of the gantry. To fit the curvature of the beam pipe 102, the magnets 108 can be somewhat arc-shaped or wedge-shaped when viewed in a direction perpendicular to the path of the beam pipe 102. However, in this case, there is no negative bending of the particles, as described above, but only positive bending by the two bending dipole magnets (B) 110.

Referring specifically to FIGS. 15-18, each magnet 108 is a fixed-field permanent magnet made from a plurality of wedge-shaped or arc-shaped segments 116 arranged around a radial center 118 of the magnet. When assembled around the beam pipe 102, the radial center 118 of each magnet is aligned with the center 103 of the beam pipe. The segments 116 are made from a ferromagnetic material, such as a sintered compound of Neodymium-Iron-Boron ($Nd_2Fe_{14}B$) or rare earth cobalt (REC), and each segment has a fixed magnetic field oriented in a predetermined direction upon manufacture of the segment. For example, certain segments 116a are fabricated with a fixed magnetic field pointing in a direction from the inner radius 120 of the segment toward the outer radius 122 of the segment, while other segments 116b are fabricated with a fixed magnetic field pointing in the opposite direction from the outer radius 122 of the segment toward the inner radius 120 of the segment. Other segments 116c are fabricated with a fixed magnetic field pointing in a direction from one lateral side 124 of the segment toward the opposite side, while still other segments 116d are fabricated with fixed magnetic fields pointing in a direction somewhere in between the directions described above.

Figure 15:
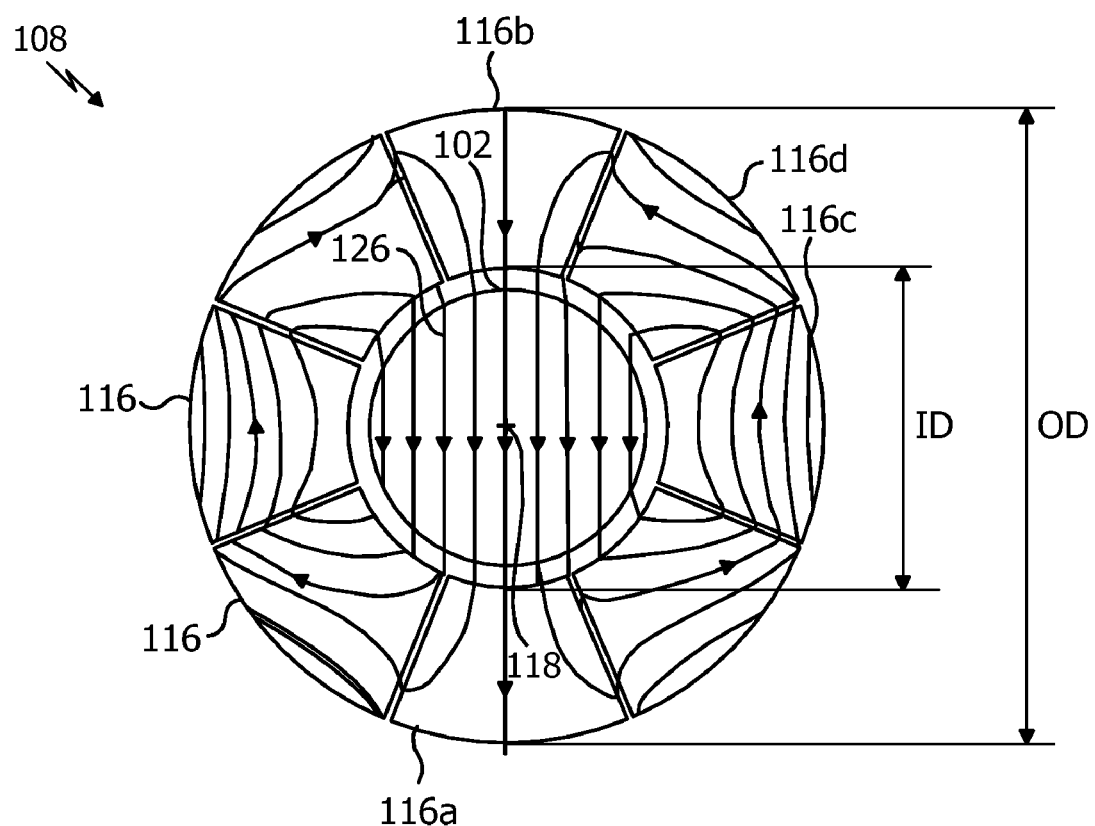
FIG. 15 is a cross-sectional view of the dipole bending magnet shown in FIG. 14, taken along line 15-15.
Figure 17:
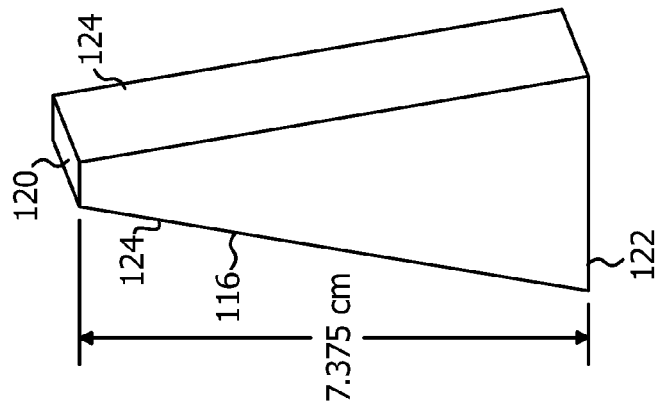
FIG. 17 shows one of the magnet segments of the quadrupole magnet shown in FIG. 16.
Figure 16:
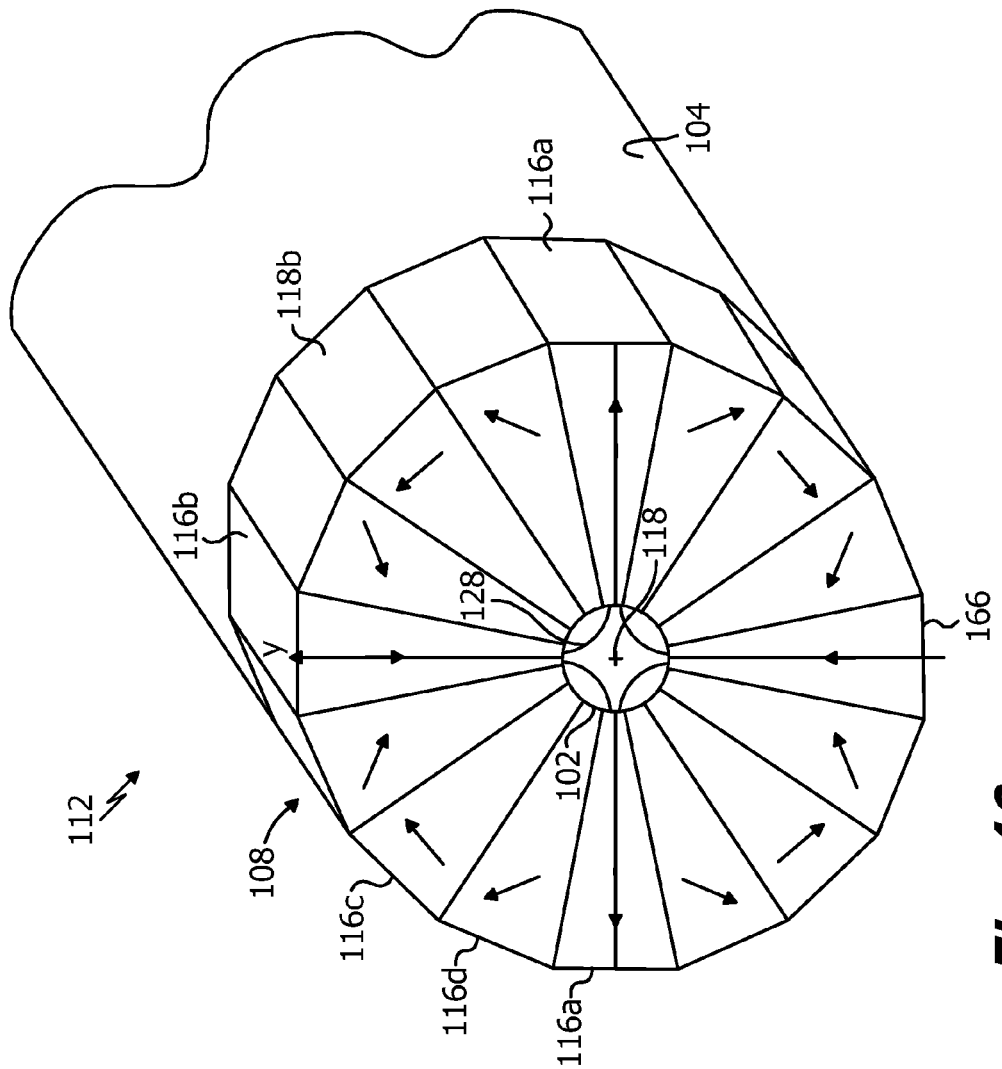
FIG. 16 is a cross-sectional view of the quadrupole defocusing magnet shown in FIG. 14, taken along line 16-16.
Figure 18:
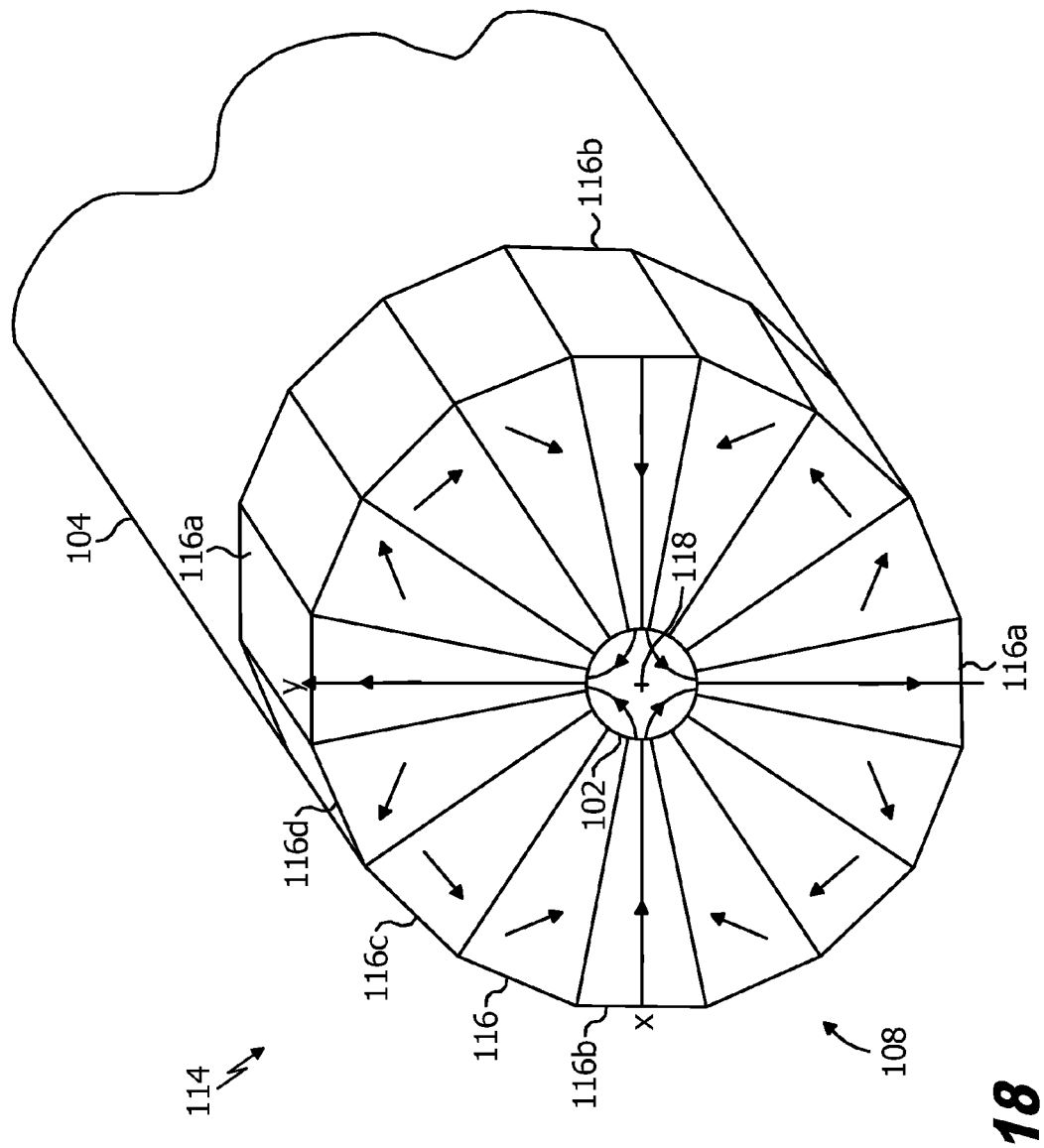
FIG. 18 is a cross-sectional view of the quadrupole focusing magnet shown in FIG. 14, taken along line 18-18.

The segments 116 are oriented around the magnet center 118 so as to produce a dipole magnet 110, as shown in FIG. 15, or a quadrupole magnet 112, 114, as shown in FIGS. 16 and 18. More specifically, the segments 116 are assembled together so that the individual magnetic field orientations of each segment combine together to produce a magnet having a resultant magnetic field oriented in a desired direction. Thus, a dipole bending magnet 110 can be formed by arranging eight segments 116 to produce a combined dipole magnetic field 126 across the magnet center 118, as shown in FIG. 15, while a quadrupole magnet 112, 114 can be formed by arranging sixteen segments 116 to produce a quadrupole magnetic field 128 across the magnet center 118, as shown in FIGS. 16 and 18. Such fixed-field permanent magnets are known in the art as "Halbach" magnets and are described in Halbach, "Design of Permanent Multipole Magnets With Oriented Rare Earth Cobalt Material," Nuclear Instruments and Methods 169, pp. 1-10 (1980), which is incorporated herein by reference in its entirety for all purposes.

The focusing or defocusing function of the quadrupole magnets 112, 114 is determined by how the respective quadrupole magnet is rotated with respect to the beam tube center 103. Thus, if a quadrupole magnet is oriented about the beam tube center 103 so that a quadrupole magnetic field flowing from a vertical direction to a horizontal direction is produced, as shown in FIG. 16, a defocusing magnet 112 is provided along the gantry 100. Conversely, if the same quadrupole magnet is rotated ninety degrees with respect to the beam tube center 103, such that the magnetic field now flows from a horizontal direction toward a vertical direction, as shown in FIG. 18, a focusing magnet 114 is provided along the orbital path of the beam pipe 102.

Referring also to FIG. 14, the magnet properties of the preferred embodiment of the unit cell 106 are set forth in the following table.

| | |
|---|---|
| $B_r$ | 1.35 T |
| $B_g$ = Br ln (OD/ID) | 2.4 T |
| OD | 17.75 cm |
| ID | 3.0 cm |
| ln (OD/ID) | 1.78 |
| QLD | 8.0 cm |
| BL | 4.8 cm |
| QLF | 11 cm |
| GF | 2.4 T/0.015 m = 160.0 T/m |
| GD | −2.4 T/0.013 m = −180.0 T/m |

Figure 20:
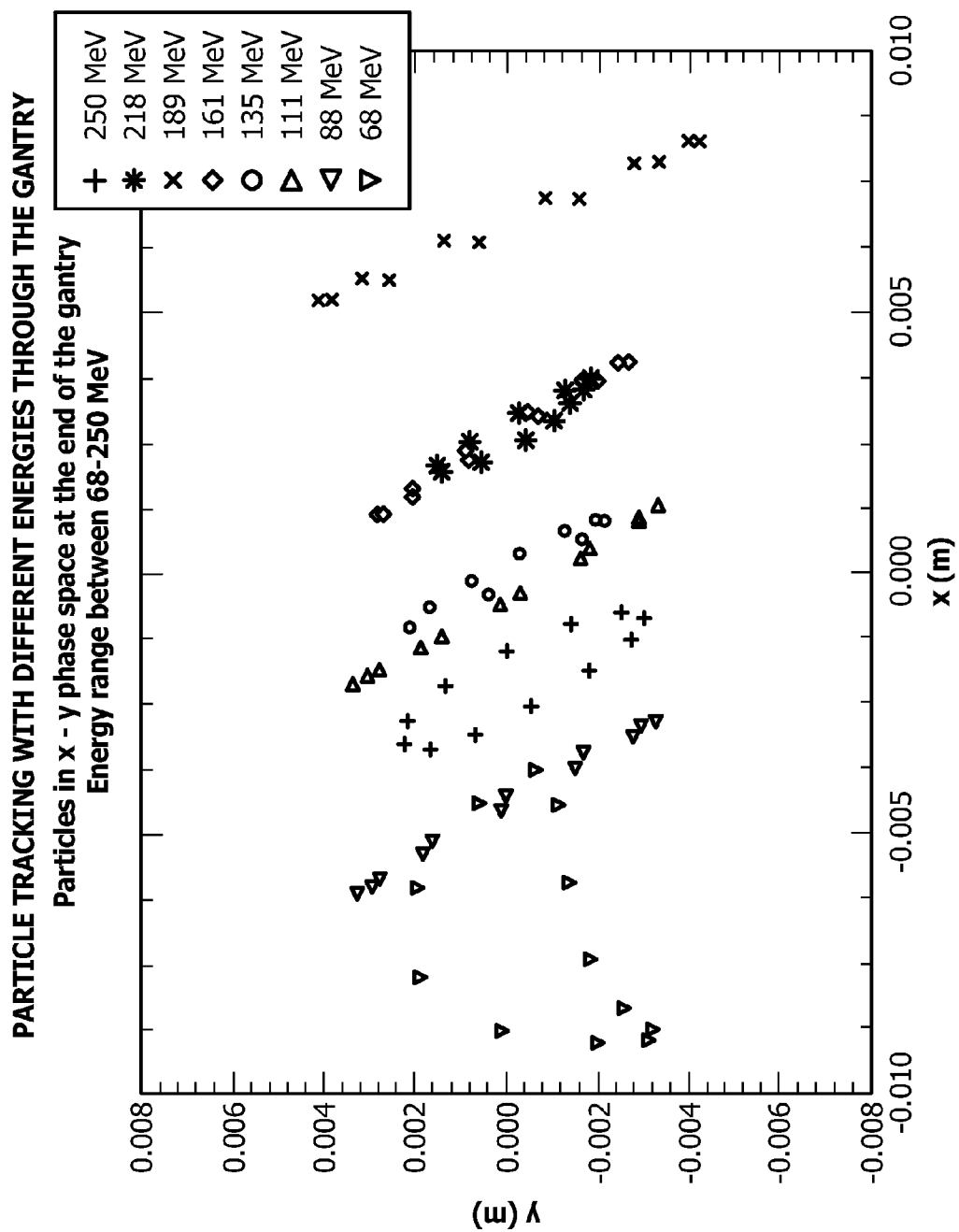
FIG. 20 is a graph showing the particle tracking of protons with different energies through the gantry according to the alternative embodiment of the present invention.

FIG. 19 also shows proton traces magnified twenty-five times, with energies in a range of between 68-250 MeV. Tracking results for particles in this energy range are shown in more detail in FIG. 20.

Thus, with the separate function magnet embodiment for a proton gantry application, the maximum achievable magnetic field is between about 2.2 to about 2.6 Tesla, and the working energy range for proton energy is between about 68 to about 250 MeV. This is due in part to the segmented structure of the fixed-field permanent magnets. Specifically, the segments of the fixed-field magnet are arranged in such a way that each segment adds to the magnetic field in a supplemental manner, resulting in a magnet with a magnetic field greater than the magnetic flux of the magnet material of its individual parts. As a result, the magnets themselves can be made smaller whereby more magnet cells can be used in a fixed space. More magnet cells increases the focusing strength of the gantry, which in turn reduces the aperture sizing of the gantry nozzle. This allows for a wider momentum energy range of particles for different medical applications.

As a result, a simple and easy to assemble magnet unit cell 106 can be provided for the gantry 100. Specifically, in the combined function magnet triplet embodiment described above, wherein the particle bending function is provided by the curvature of the magnet, each magnet must be precisely positioned to match the curvature of the beam tube. This is further complicated when positive and negative bending magnets are used. With this separate function magnet embodiment, wherein the bending function is achieved by the dipole magnetic field produced by the dipole magnet, matching the curvature of the magnet to the curvature of the beam tube is less critical.

However, similar to that described above with respect to the combined function magnet triplet cells, modifications of the unit cell may be necessary to fully assemble the gantry. For example, at the transition point 130 of the gantry 100 of this alternative embodiment, where the beam pipe 102 reverses its curvature, and/or at the beam entry point 132 and/or at the beam exit point 134, modifications of the unit cell 106 can be utilized to provide the desired bending and focusing/defocusing functions. For example, a half cell consisting of a single bending dipole magnet 110 and a reduced length, defocusing magnet 112 can be utilized at the beam entry point 132 and/or the beam exit point 134 of the gantry 100 to achieve the desired bend angle and focusing at these points. Similarly, at the beam pipe curvature transition point 130, two half-cells, as described above, can be assembled together in a juxtaposed orientation to form a "straight" magnet cell.

As a result of the present invention, the size of the gantry in a particle therapy facility can be dramatically reduced and the control system for a gantry treatment room can be greatly simplified. Specifically, the gantry 24, 100 can be made about 20 meters long, from the rotation point 32 to the iso-center 34, with a height of about 3.2 meters. Also, the advantages of using permanent magnets include a reduction in the number of DC power supplies. Moreover, a very strong focusing structure is obtained by using small size "Halbach" magnets.

Although preferred embodiments of the present invention have been described herein with reference to the accompanying drawings, it is to be understood that the invention is not limited to those precise embodiments and that various other changes and modifications may be affected herein by one skilled in the art without departing from the scope or spirit of the invention, and that it is intended to claim all such changes and modifications that fall within the scope of the invention.

The invention claimed is:

1. A particle therapy gantry for delivering a particle beam to a patient comprising:
   a beam tube having a curvature defining a particle beam path; and
   a plurality of fixed field permanent magnets sequentially arranged along said beam tube for guiding the particle beam along said particle path, wherein said fixed field permanent magnets are arranged in a series of unit cells, each cell comprising two bending dipole magnets, a focusing quadrupole magnet and two defocusing quadrupole magnets, said bending dipole magnets performing the function of bending the particle beam along said particle beam path, said focusing quadrupole magnet performing the function of focusing the particle beam along said particle beam path and said defocusing quadrupole magnets performing the function of defocusing the particle beam along said particle beam path.

2. A gantry as defined in claim 1, wherein said bending dipole magnets are separated by said defocusing quadrupole magnet and flanked by said focusing quadrupole magnet.

3. A gantry as defined in claim 2, wherein said unit cell is symmetric with respect to the longitudinal center of said defocusing quadrupole magnet.

4. A gantry as defined in claim 1, wherein said defocusing quadrupole magnet has a linear horizontal defocusing gradient, whereby particles of the beam path tend to disperse along a plane defined by a radius of curvature of said beam tube, but tend to concentrate with respect to a plane perpendicular to said radius of curvature, and wherein said two focusing quadrupole magnets have a linear horizontal focusing gradient, whereby particles tend to concentrate along said plane defined by said radius of curvature of said beam tube, but tend to disperse along said plane perpendicular to said plane defined by said radius of curvature of said beam tube.

5. A gantry as defined in claim 1, wherein said fixed field permanent magnets each comprise a plurality of ferromagnetic segments radially arranged around a magnet center, each segment having a fixed magnetic field oriented in a predetermined direction.

6. A gantry as defined in claim 5, wherein each of said bending dipole magnet comprises eight of said segments arranged to produce a combined dipole magnetic field across said magnet center, and wherein each of said quadrupole magnets comprise sixteen of said segments arranged to produce a quadrupole magnetic field across said magnet center.

7. A gantry as defined in claim 5, wherein said beam tube has a radial center line, and wherein each of said defocusing quadrupole magnets is rotated about said beam tube center line to produce a quadrupole magnetic field flowing from a plane perpendicular to a plane defined by a radius of curvature of said beam tube to said plane defined by said radius of curvature of said beam tube, and wherein each of said focusing quadrupole magnets is rotated about said beam tube center ninety degrees with respect to said defocusing quadrupole magnets to produce a quadrupole magnetic field flowing from said plane defined by said radius of curvature of said beam tube to said plane perpendicular to said plane defined by said radius of curvature of said beam tube.

8. A gantry as defined in claim 1, wherein said beam tube includes a particle beam entry point, a transition point, a particle beam exit point, a first curved particle beam path arc length extending between said entry point and said transition point and a second curved particle beam path arc length extending between said transition point and said exit point, said first arc length bending about ninety degrees and said second arc length bending about one hundred eighty degrees in a direction opposite said first arc length.

9. A gantry as defined in claim 8, wherein said fixed field magnets comprise two half-cells disposed in juxtaposed orientation at said beam tube transition point, a half-cell disposed at said beam tube entry point and a half-cell disposed at said beam tube exit point, each of said half-cells comprising a bending dipole magnet, a defocusing quadrupole magnet and a focusing quadrupole magnet.

10. A particle beam therapy system comprising:
    a source of particles;
    an accelerator for accelerating the particles as a particle beam;
    an injector for transporting particles from said source to said accelerator;
    a patient treatment station including a rotatable gantry for delivering a particle beam to a patient, said gantry including a beam tube having a curvature defining a particle beam path and a plurality of fixed field permanent magnets sequentially arranged along said beam tube for guiding the particle beam along said particle path; and
    a beam transport system for transporting the accelerated beam from said accelerator to said patient treatment station,
    wherein said fixed field permanent magnets of said gantry are arranged in a series of unit cells, each cell comprising two bending dipole magnets, a focusing quadrupole magnet and two defocusing quadrupole magnets, said bending dipole magnets performing the function of bending the particle beam along said particle beam path, said focusing quadrupole magnet performing the function of focusing the particle beam along said particle beam path and said defocusing quadrupole magnets performing the function of defocusing the particle beam along said particle beam bath.

11. A particle beam therapy system as defined in claim 10, wherein said bending dipole magnets are separated by said defocusing quadrupole magnet and flanked by said focusing quadrupole magnet.

12. A particle beam therapy system as defined in claim 10, wherein said defocusing quadrupole magnet has a linear horizontal defocusing gradient, whereby particles of the beam path tend to disperse along a plane defined by a radius of curvature of said beam tube, but tend to concentrate with respect to a plane perpendicular to said radius of curvature, and wherein said two focusing quadrupole magnets have a linear horizontal focusing gradient, whereby particles tend to concentrate along said plane defined by said radius of curvature of said beam tube, but tend to disperse along said plane perpendicular to said plane defined by said radius of curvature of said beam tube.

13. A particle beam therapy system as defined in claim 10, wherein said fixed field permanent magnets each comprise a plurality of ferromagnetic segments radially arranged around a magnet center, each segment having a fixed magnetic field oriented in a predetermined direction.

14. A particle beam therapy system as defined in claim 13, wherein each of said bending dipole magnet comprises eight of said segments arranged to produce a combined dipole magnetic field across said magnet center, and wherein each of said quadrupole magnets comprise sixteen of said segments arranged to produce a quadrupole magnetic field across said magnet center.

15. A particle beam therapy system as defined in claim 13, wherein said beam tube has a radial center line, and wherein each of said defocusing quadrupole magnets is rotated about said beam tube center line to produce a quadrupole magnetic field flowing from a plane perpendicular to a plane defined by a radius of curvature of said beam tube to said plane defined by said radius of curvature of said beam tube, and wherein each of said focusing quadrupole magnets is rotated about said beam tube center ninety degrees with respect to said defocusing quadrupole magnets to produce a quadrupole magnetic field flowing from said plane defined by said radius of curvature of said beam tube to said plane perpendicular to said plane defined by said radius of curvature of said beam tube.

16. A particle therapy gantry for delivering a particle beam to a patient comprising:

a beam tube having a curvature defining a particle beam path; and a plurality of fixed field permanent magnets sequentially arranged along said beam tube for guiding the particle beam along said particle path, wherein each of said fixed field permanent magnets is a separate function magnet performing only one of a bending function, a focusing function and a defocusing function along said particle path.

17. A method for delivering a particle beam to a patient through a gantry comprising the steps of:

bending the particle beam with a plurality of fixed field permanent magnets sequentially arranged along a beam tube of the gantry, the particle beam traveling in said beam tube;

alternately focusing and defocusing the particle beam traveling in said beam tube with alternately arranged focusing and defocusing fixed field permanent magnets; and delivering said particle beam from said gantry to a patient, wherein said beam is strongly focused in both the horizontal and vertical planes, wherein said fixed field permanent magnets are arranged in a series of unit cells, each cell comprising two bending dipole magnets, a focusing quadrupole magnet and two defocusing quadrupole magnets, said bending dipole magnets performing the function of bending the particle beam along said particle beam path, said focusing quadrupole magnet performing the function of focusing the particle beam along said particle beam path and said defocusing quadrupole magnets performing the function of defocusing the particle beam along said particle beam path.

* * * * *